Figure 1:
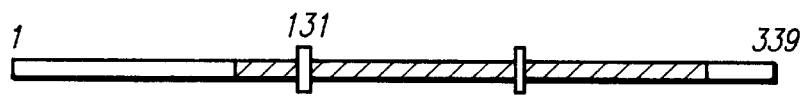

United States Patent [19]
Hasty

[11] Patent Number: 6,057,104
[45] Date of Patent: May 2, 2000

[54] DISRUPTION OF THE MAMMALIAN RAD51 PROTEIN AND DISRUPTION OF PROTEINS THAT ASSOCIATE WITH MAMMALIAN RAD51 FOR HINDERING CELL PROLIFERATION

[75] Inventor: Paul Hasty, The Woodlands, Tex.

[73] Assignee: Lexicon Genetics Incorporated, The Woodlands, Tex.

[21] Appl. No.: 08/964,614

[22] Filed: Nov. 5, 1997

Related U.S. Application Data

[63] Continuation-in-part of application No. 08/758,280, Nov. 5, 1996.

[51] Int. Cl.$^7$ .................................................. C12Q 1/68
[52] U.S. Cl. .............................. 435/6; 435/196; 530/350; 536/23.2; 536/23.5
[58] Field of Search ........................ 435/6, 196; 530/350; 536/23.2, 23.5

[56] References Cited

U.S. PATENT DOCUMENTS

| | | | |
|---|---|---|---|
| 4,016,100 | 4/1977 | Suzuki et al. | 264/4.3 |
| 4,190,496 | 2/1980 | Rubenstein et al. | 435/7.9 |
| 4,311,712 | 1/1982 | Evans et al. | 514/773 |
| 4,370,349 | 1/1983 | Evans et al. | 514/785 |
| 4,372,949 | 2/1983 | Kodama et al. | 514/78 |
| 4,452,747 | 6/1984 | Gersonde et al. | 264/4.1 |
| 4,529,561 | 7/1985 | Hunt et al. | 264/4.3 |
| 4,725,442 | 2/1988 | Haynes | 424/490 |
| 4,737,323 | 4/1988 | Martin et al. | 264/4.3 |
| 4,920,016 | 4/1990 | Allen et al. | 424/1.21 |
| 4,921,706 | 5/1990 | Roberts et al. | 424/450 |
| 4,927,637 | 5/1990 | Morano et al. | 424/450 |
| 4,944,948 | 7/1990 | Uster et al. | 424/450 |
| 5,008,050 | 4/1991 | Cullis et al. | 264/4.3 |
| 5,009,956 | 4/1991 | Baumann | 428/402.2 |
| 5,316,931 | 5/1994 | Donson et al. | 435/172.3 |
| 5,424,186 | 6/1995 | Fodor et al. | 435/6 |
| 5,529,774 | 6/1996 | Barba et al. | 424/93.21 |

OTHER PUBLICATIONS

Gura, *Science,* vol. 278, 1997, pp. 1041–1042, Nov. 7, 1997.
Aboussekhra et al., 1992, "Semidominant Suppressors of Srs2 Helicase Mutations of *Saccharomyces cerevisiae* Map in the RAD51 Gene, Whose Sequence Predicts a Protein with Similarities to Procaryotic RecA Proteins," *Mol. Cell. Biol.* 12:3224–3234.
Ashley et al., 1995, "Dynamic changes in Rad51 distribution on chromatin during meiosis in male and female vertebrates," *Chromosoma* 104:19–28.
Baker et al., 1990, "Suppression of Human Colorectal Carcinoma Cell Growth by Wild–Type p53," *Science* 249:912–915.
Bennett et al., 1993, "Lethality induced by a single site–specific double–strand break in a dispensable yeast plasmid," *Proc. Natl. Acad. Sci. U.S.A.* 90:5613–5617.
Benson et al., 1994, "Purification and characterization of the human Rad51 protein, an analogue of *E. coli* RecA," *EMBO Journal* 13:5764–5771.

Bezzubova et al., 1993, "A chicken RAD51 homologue is expressed at high levels in lymphoid and reproductive organs," *Nucleic Acids Res.* 21:1577–1580.
Bishop, 1994, "RecA Homologs Dmc1 and Rad51 Interact to Form Multiple Nuclear Complexes Prior to Meiotic Chromosome Synapsis," *Cell* 79:1081–1092.
Bradley et al., 1992, "Modifying the Mouse: Design and Desire," *Bio/Technology* 10:534–539.
Carr and Hoekstra, 1995, "The cellular responses to DNA damage," *Trends in Cell Biology* 5:32–40.
Cleaver, 1994, "It Was a Very Good Year for DNA Repair," *Cell* 76:1–4.
Derossi et al., 1994, "The Third Helix of the Antennapedia Homeodomain Translocates through Biological Membranes," *J. Biol. Chem.* 269:10444–10450.
Donehower et al., 1992, "Mice deficient for p53 are developmentally normal but susceptible to spontaneous tumours," *Nature* 356:215–221.
Donovan et al., 1994, "Homotypic and heterotypic protein associations control Rad51 function in double–strand break repair," *Genes and Develop.* 8:2552–2562.
Gallop et al., 1994, "Applications of Combinatorial Technologies to Drug Discovery. 1. Background and Peptide Combinatorial Libraries," *J. Med. Chem.* 37:1233–1251.
Gordon et al., 1994, "Applications of Combinatorial Technologies to Drug Discovery. 2. Combinatorial Organic Synthesis, Library Screening Strategies, and Future Directions," *J. Med. Chem.* 37:1385–1401.
Haaf et al., 1995, "Nuclear foci of mammalian Rad51 recombination protein in somatic cells after DNA damage and its localization in symanptonemal complexes," *Proc. Natl. Acad. Sci. U.S.A.* 92:2298–2302.
Habu et al., 1996, "The mouse and human homologs of DMC1, the yeast meiosis–specific homologous recombination gene, have a common unique form of exon–skipped transcript in meiosis," *Nucleic Acids Res.* 24:470–477.

(List continued on next page.)

*Primary Examiner*—James Ketter
*Attorney, Agent, or Firm*—Pennie & Edmonds LLP

[57] ABSTRACT

When a mutation, designated rad51$^{M1}$, was generated in the mouse MmRAD51 gene, mutant embryos died shortly after implantation. rad51$^{M1}$ cells exhibited hypersensitivity to ionizing radiation, reduced proliferation, programmed cell death and chromosome loss. The disruption of MmRad51 protein—protein interactions stopped cell proliferation and/or reduced cell viability. Several proteins that interact with MmRad51 have been identified including, for example Brca2 and M96. Additionally, Rad51 self-associates via the N-terminal region. When a single residue was changed from a conserved lysine to an alanine, the alteration proved toxic to cells. Moreover, a rad51 allele that lacked the RecA homology region was also deleterious to cells. In view of the above, it is clear that inhibiting MmRad51 function or the function of any molecule that associates with MmRad51, or any molecule in the Rad51 or Rad52 pathways, hinders cell proliferation and/or viability. Accordingly, molecules capable of blocking these critical DNA repair pathways may be effective as therapeutics for inhibiting cell proliferation.

12 Claims, 3 Drawing Sheets

OTHER PUBLICATIONS

Harper et al., 1993, "The p21 Cdk–Interacting Protein Cip1 Is a Potent Inhibitor of G1 Cyclin–Dependent Kinases," *Cell* 75:805–816.

Harvey et al., 1993, "In vitro growth characteristics of embryo fibroblasts isolated from p53–deficient mice," *Oncogene* 8:2457–2467.

Hasty et al., 1992, "The Role and Fate of DNA Ends for Homologous Recombination in Embryonic Stem Cells," *Mol. Cell. Biol.* 12:2464–2474.

Hays et al., 1995, "Complex formation in yeast double–strand break repair: Participation of Rad51, Rad52, Rad55 and Rad57 proteins," *Proc. Natl. Acad. Sci. U.S.A.* 92:6925–6929.

Horii et al., 1992, "Inhibitory Effects of N– and C–terminal Truncated *Escherichia coli* recA Gene Products on Functions of the Wild–type recA Gene," *J. Mol. Biol.* 223:105–114.

Inouye et al., 1994, "Isolation of cDNA Encoding a Metal Response Element Binding Protein Using a Novel Expression Cloning Procedure: The One Hybrid System," *DNA Cell. Biol.* 13(7):731–742.

Jang et al., 1994, "Cloning and sequence analysis of rhp51$^+$, a *Schizosaccharomyces pombe* homolog of the *Saccharomyces cerevisiae* RAD51 gene," *Gene* 142:207–211.

Jeggo, 1990, "Studies on mammalian mutants defective in rejoining double–strand breaks in DNA," *Mutation Research* 239:1–16.

Johnson and Symington, 1995, "Functional Differences and Interactions among the Putative RecA Homologs Rad51, Rad55, and Rad57," *Mol. Cell. Biol.* 15:4843–4850.

Kastan et al., 1991, "Participation on p53 Protein in the Cellular Response to DNA Damage," *Cancer Research* 51:6304–6311.

Kirchgessner et al., 1995, "DNA–Dependent Kinase (P350) as a Candidate Gene for the Murine SCID Defect," *Science* 267:1178–1183.

Ko and Prives, 1996, "p53: puzzle and paradigm," *Genes and Develop.* 10:1054–1072.

Krasin and Hutchinson, 1977, "Repair of DNA Double–strand Breaks in *Escherichia coli*, which Requires recA Function and the Presence of a Duplicate Genome," *J. Mol. Biol.* 116:81–98.

Kuerbitz et al., 1992, "Wild–type p53 is a cell cycle checkpoint determinant following irradiation," *Proc. Natl. Acad. Sci. U.S.A.* 89:7491–7495.

Liang et al., 1996, "Chromosomal double–strand break repair in Ku80–deficient cells," *Proc. Natl. Acad. Sci. U.S.A.* 93:8929–8933.

Lim and Hasty, 1996, "A mutation in mouse rad51 results in an early embryonic lethal that is suppressed by a mutation in p53," *Mol. Cell. Biol.* 16(12):7133–7143.

Lowe et al., 1994, "p53 Status and the Efficacy of Cancer Therapy in Vivo," *Science* 266:807–810.

Lu and Lane, 1993, "Differential Induction of Transcriptionally Acive p53 Following UV or Ionizing Radiation: Defects in Chromosome Instability Syndromes?" *Cell* 75:765–778.

Malkova et al., 1996, "Double–strand break repair in the absence of RAD51 in yeast: A possible role for break–induced DNA replication," *Proc. Natl. Acad. Sci. U.S.A.* 93:7131–7136.

Melton et al., 1984, "Structure, expression, and mutation of the hypoxanthine phosphoribosyltransferase gene," *Proc. Natl. Acad. Sci. U.S.A.* 81:2147–2151.

Milne and Weaver, 1993, "Dominant negative alleles of RAD52 reveal a DNA repair/recombination complex including Rad51 and Rad52," *Genes and Develop.* 7:1755–1765.

Morita et al., 1993, "A mouse homolog of the *Escherichia coli* recA and *Saccharomyces cerevisiae* RAD51 genes," *Proc. Natl. Acad. Sci. U.S.A.* 90:6577–6580.

Mortimer, 1958, "Radiobiological and Genetic Studies on a Polyploid Series (Haploid to Hexaploid) of *Saccharomyces cerevisiae*," *Radiat. Res.* 9:312–326.

Muris et al., 1993, "Cloning the RAD51 homologue of *Schizosaccharomyces pombe*," *Nucleic Acids Res.* 21:4586–4591.

Norioka et al., 1995, "Two recA Genes in *Myxococcus xanthus*," *J. Bacteriol.* 177:4179–4182.

Nussenzweig et al., 1996, "Requirement for Ku80 in growth and immunoglobulin V(D)J recombination," *Nature* 382:551–555.

Ogawa et al., 1993, "Similarity of the Yeast RAD51 Filament to the Bacterial RecA Filament," *Science* 259:1896–1899.

Park et al., 1996, "Physical Interaction between Human Rad52 and RPA Is Required for Homologous Recombination in Mammalian Cells," *J. Biol. Chem.* 1996:18996–19000.

Resnick et al., 1989, "Lack of DNA homology in a pair of divergent chromosomes greatly sensitizes them to loss by DNA damage," *Proc. Natl. Acad. Sci. U.S.A.* 86:2276–2280.

Rockmill et al., 1995, "Roles for two RecA homologs in promoting meiotic chromosome synapsis," *Genes and Develop.* 9:2684–2695.

Roth et al., 1995, "How to make ends meet," *Current Biology* 5:496–499.

Rouet et al., 1994, "Introduction of Double–Strand Breaks into the Genome of Mouse Cells by Expression of a Rare–Cutting Endonuclease," *Mol. Cell. Biol.* 14:8096–8106.

Schiestl et al., 1989, "Cloning and Sequence Analysis of the *Saccharomyces cerevisiae* RAD9 Gene and Further Evidence that Its Product is Required for Cell Cycle Arrest Induced by DNA Damage," *Mol. Cell. Biol.* 9:1882–1896.

Schlissel et al., 1993, "Double–strand signal sequence breaks in V(D)J recombination are blunt, 5'–phosphorylated, RAG–dependent, and cell cycle regulated," *Genes and Develop.* 7:2520–2532.

Shen et al., 1996, "Specific Interactions between the Human RAD51 and RAD52 Proteins," *J. Biol. Chem.* 271:148–152.

Shinohara et al., 1992, "Rad51 Protein Involved in Repair and Recombination in *S. cerevisiae* Is a RecA–like Protein," *Cell* 69:457–470.

Shinohara et al., 1993, "Cloning of human, mouse and fission yeast recombination genes homologous to RAD51 and recA," *Nature Genet.* 4:239–43.

Songyang et al., 1993, "SH2 Domains Recognize Specific Phosphopeptide Sequences," *Cell* 72:767–778.

Story et al., 1992, "The structure of the *E. coli* recA protein monomer and polymer," *Nature* 355:318–325.

Story et al., 1993, "Structural Relationship of Bacterial RecA Proteins to Recombination Proteins from Bacteriophage T4 and Yeast," *Science* 259:1892–1896.

Sugawara et al., 1995, "DNA structure–dependent requirements for yeast RAD genes in gene conversion," *Nature* 373:84–86.

Sung, 1994, "Catalysis of ATP–Dependent Homologous DNA Pairing and Strand Exchange by Yeast RAD51 Protein," *Science* 265:1241–1243.

Sung and Robberson, 1995, "DNA Strand Exchange Mediated by a RAD51–ssDNA Nucleoprotein Filament with Polarity Opposite to That of RecA," *Cell* 82:453–461.

Symonds et al., 1994, "p53–Dependent Apoptosis Suppresses Tumor Growth and Progression in Vivo," *Cell* 78:703–711.

Tateishi et al., 1992, "C–terminal Truncated *Escherichia coli* RecA Protein RecA5327 Has Enhanced Binding Affinities to Single– and Double–Stranded DNAs," *J. Mol. Biol.* 223:115–129.

Tavtigian et al., 1996, "The complete BRCA2 gene and mutations in chromosome 13q–linked kindreds," *Nature Gen.* 12:333–337.

Terasawa et al., 1995, "Localization of RecA–like recombination proteins on chromosomes of the lily at various meiotic stages," *Genes and Develop.* 9:925–934.

Tsuzuki et al., 1996, "Targeted disruption of the Rad51 gene leads to lethality in embryonic mice," *Proc. Natl. Acad. Sci. U.S.A.* 93:6236–6240.

Vogelstein, 1990, "A deadly inheritance," *Nature* 348:681–682.

Weinert and Hartwell, 1988, "The RAD9 Gene Controls the Cell Cycle Response to DNA Damage in *Saccharomyces cerevisiae*," *Science* 241:317–322.

Wooster et al., 1995, "Identification of the breast cancer susceptibility gene BRCA2," *Nature* 378:789–792.

Yamamoto et al., 1996, "Cell cycle–dependent expression of the mouse Rad51 gene in proliferating cells," *Mol. Gen. Genet.* 251:1–12.

Yarranton and Sedgwick, 1982, "Cloned Truncated recA Genes in *E. coli:* II. Effects of Truncated Gene Products on in vivo recA$^+$ Protein Activity," *Mol. Gen. Gent.* 185:99–104.

Yoshimura et al., 1993, "Cloning and sequence of the human RecA–like gene cDNA," *Nucleic Acids Res.* 21:1665.

Zhu et al., 1996, "Ku86–Deficient Mice Exhibit Severe Combined Immunodeficiency and Defective Processing of V(D)J Recombination Intermediates," *Cell* 86:379–389.

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 339 amino acids
      (B) TYPE: amino acid
      (C) STRANDEDNESS: single
      (D) TOPOLOGY: linear (ii) MOLECULE TYPE: None (xi) SEQUENCE DESCRIPTION: SEQ ID NO:1:

```
Met Ala Met Gln Met Gln Leu Glu Ala Ser Ala Asp Thr Ser Val Glu
 1               5                  10                  15

Glu Glu Ser Phe Gly Pro Gln Pro Ile Ser Arg Leu Glu Gln Cys Gly
            20                  25                  30

Ile Asn Ala Asn Asp Val Lys Lys Leu Glu Glu Ala Gly Tyr His Thr
        35                  40                  45

Val Glu Ala Val Ala Tyr Ala Pro Lys Lys Glu Leu Ile Asn Ile Lys
50                  55                  60

Gly Ile Ser Glu Ala Lys Ala Asp Lys Ile Leu Thr Glu Ala Ala Lys
65                  70                  75                  80

Leu Val Pro Met Gly Phe Thr Thr Ala Thr Glu Phe His Gln Arg Arg
                85                  90                  95

Ser Glu Ile Ile Gln Ile Thr Thr Gly Ser Lys Glu Leu Asp Lys Leu
            100                 105                 110

Leu Gln Gly Gly Ile Glu Thr Gly Ser Ile Thr Glu Met Phe Gly Glu
        115                 120                 125

Phe Arg Thr Gly Lys Thr Gln Ile Cys His Thr Leu Ala Val Thr Cys
130                 135                 140

Gln Leu Pro Ile Asp Arg Gly Gly Gly Glu Gly Lys Ala Met Tyr Ile
145                 150                 155                 160

Asp Thr Glu Gly Thr Phe Arg Pro Glu Arg Leu Leu Ala Val Ala Glu
                165                 170                 175

Arg Tyr Gly Leu Ser Gly Ser Asp Val Leu Asp Asn Val Ala Tyr Ala
            180                 185                 190

Arg Gly Phe Asn Thr Asp His Gln Thr Gln Leu Leu Tyr Gln Ala Ser
        195                 200                 205

Ala Met Met Val Glu Ser Arg Tyr Ala Leu Leu Ile Val Asp Ser Ala
210                 215                 220

Thr Ala Leu Tyr Arg Thr Asp Tyr Ser Gly Arg Gly Glu Leu Ser Ala
225                 230                 235                 240

Arg Gln Met His Leu Ala Arg Phe Leu Arg Met Leu Leu Arg Leu Ala
                245                 250                 255

Asp Glu Phe Gly Val Ala Val Val Ile Thr Asn Gln Val Val Ala Gln
            260                 265                 270

Val Asp Gly Ala Ala Met Phe Ala Ala Asp Pro Lys Lys Pro Ile Gly
        275                 280                 285

Gly Asn Ile Ile Ala His Ala Ser Thr Thr Arg Leu Tyr Leu Arg Lys
290                 295                 300

Gly Arg Gly Glu Thr Arg Ile Cys Lys Ile Tyr Asp Ser Pro Cys Leu
305                 310                 315                 320
```

-continued

```
Pro Glu Ala Glu Ala Met Phe Ala Ile Asn Ala Asp Gly Val Gly Asp
                325                 330                 335

Ala Lys Asp
```

(2) INFORMATION FOR SEQ ID NO:2:

(i) SEQUENCE CHARACTERISTICS:
        (A) LENGTH: 339 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:2:

```
Met Ala Met Gln Met Gln Leu Glu Ala Asn Ala Asp Thr Ser Val Glu
 1               5                  10                  15

Glu Glu Ser Phe Gly Pro Gln Pro Ile Ser Arg Leu Glu Gln Cys Gly
                20                  25                  30

Ile Asn Ala Asn Asp Val Lys Lys Leu Glu Glu Ala Gly Phe His Thr
                35                  40                  45

Val Glu Ala Val Ala Tyr Ala Pro Lys Lys Glu Leu Ile Asn Ile Lys
 50                  55                  60

Gly Ile Ser Glu Ala Lys Ala Asp Lys Ile Leu Ala Glu Ala Ala Lys
 65                  70                  75                  80

Leu Val Pro Met Gly Phe Thr Thr Ala Thr Glu Phe His Gln Arg Arg
                85                  90                  95

Ser Glu Ile Ile Gln Ile Thr Thr Gly Ser Lys Glu Leu Asp Lys Leu
                100                 105                 110

Leu Gln Gly Gly Ile Glu Thr Gly Ser Ile Thr Glu Met Phe Gly Glu
                115                 120                 125

Phe Arg Thr Gly Lys Thr Gln Ile Cys His Thr Leu Ala Val Thr Cys
                130                 135                 140

Gln Leu Pro Ile Asp Arg Gly Gly Glu Gly Lys Ala Met Tyr Ile
145                 150                 155                 160

Asp Thr Glu Gly Thr Phe Arg Pro Glu Arg Leu Leu Ala Val Ala Glu
                165                 170                 175

Arg Tyr Gly Leu Ser Gly Ser Asp Val Leu Asp Asn Val Ala Tyr Ala
                180                 185                 190

Arg Ala Phe Asn Thr Asp His Gln Thr Gln Leu Leu Tyr Gln Ala Ser
                195                 200                 205

Ala Met Met Val Glu Ser Arg Tyr Ala Leu Leu Ile Val Asp Ser Ala
                210                 215                 220

Thr Ala Leu Tyr Arg Thr Asp Tyr Ser Gly Arg Gly Glu Leu Ser Ala
225                 230                 235                 240

Arg Gln Met His Leu Ala Arg Phe Leu Arg Met Leu Arg Leu Ala
                245                 250                 255

Asp Glu Phe Gly Val Ala Val Val Ile Thr Asn Gln Val Val Ala Gln
                260                 265                 270

Val Asp Gly Ala Ala Met Phe Ala Ala Asp Pro Lys Lys Pro Ile Gly
                275                 280                 285

Gly Asn Ile Ile Ala His Ala Ser Thr Thr Arg Leu Tyr Leu Arg Lys
                290                 295                 300

Gly Arg Gly Glu Thr Arg Ile Cys Lys Ile Tyr Asp Ser Pro Cys Leu
305                 310                 315                 320
```

```
-continued

Pro Glu Ala Glu Ala Met Phe Ala Ile Asn Ala Asp Gly Val Gly Asp
                325                 330                 335

Ala Lys Asp (2) INFORMATION FOR SEQ ID NO:3:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

Phe Leu Ser Arg Leu Pro Leu Pro Ser Pro Val Ser Pro Ile Cys Thr
1               5                   10                  15

Phe Val Ser Pro Ala Ala Gln Lys Ala Phe Gln Pro Pro Arg Ser
                20                  25                  30

(2) INFORMATION FOR SEQ ID NO:4:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

Arg Gln Ile Lys Ile Trp Phe Gln Asn Arg Arg Met Lys Trp Lys Lys
1               5                   10                  15
```

DISRUPTION OF THE MAMMALIAN RAD51 PROTEIN AND DISRUPTION OF PROTEINS THAT ASSOCIATE WITH MAMMALIAN RAD51 FOR HINDERING CELL PROLIFERATION

The present application is a continuation-in-part of and claims priority to U.S. applications Ser. Nos. 08/758,280, filed Nov. 5, 1996. The disclosure of the above application is herein incorporated by reference.

1.0. FIELD OF THE INVENTION

The present invention relates to molecules that disrupt mammalian Rad51 or Rad52 function, or disrupt the function of other molecules that are involved in the Rad51 or Rad52 pathways. Such molecules are useful as a means to hinder cell proliferation or to promote programmed cell death, and define a novel class of therapeutic agents for use in the treatment of proliferative disorders such as autoimmune disease and cancer.

2.0. BACKGROUND OF THE INVENTION

DNA repair and recombination are required by organisms to prevent the accumulation of mutations and to maintain the integrity of genetic information. Compromised genetic material may result in cell cycle arrest, programmed cell death, chromosome loss or cell senescence. Alternatively, compromised genetic information may result in dysregulation of the cell cycle ultimately leading to increased cellular growth and tumor formation.

The repair of double-strand breaks (DSB) in DNA is an essential cellular process. DSB repair may occur during general cellular functions such as DNA repair (Friedberg et al., 1995, DNA Repair and Mutagenesis. American Society for Microbiology, Washington, D.C.). In bacteria and yeast cells, DSB are predominately repaired by a homologous recombination pathway (Krasin and Hutchinson, 1977, J. Mol. Biol. 116:81–98; Mortimer, 1958, Radiat. Res. 9:312–16. In the budding yeast *Saccharomyces cerevisiae* the RAD52 epistasis group ($Rad_{50}$ to Rad57, Mre11 and Xrs2) was identified in cells sensitive to ionizing radiation (reviewed in Friedberg, 1995; Petes et al., 1991, Recombination in yeast., p. 407–521. In J. R. P. J. R. Broach, and E. W. Jones (ed.), The Molecular and Cellular Biology of the Yeast Saccharomyces. Cold Spring Harbor Laboratory Press, Cold Spring Harbor, New York). Later, some of the members of this group were shown to be important for recombinational repair (e.g., Rad51, Rad52, Rad54, Rad55, Rad57 (Malkova et al., 1996, Proc. Natl. Acad. Sci. USA 93:7131–36, Sugawara et al., 1995, Nature 373:84–86).

Among the members of the RAD52 epistasis group, ScRad51 is particularly interesting because it shares similarity with the Escherichia coli recombination protein, RecA. ScRad51 and RecA polymerize on double-stranded and single-stranded DNA (dsDNA, ssDNA) to produce a helical filament, and both enzymes catalyze an ATP-dependent strand exchange between homologous DNA molecules (Ogawa et al., 1993, Science 259:1896–99; Sung, 1994, Science 265:1241–4364; Sung and Robberson, 1995, Cell 82:453–61). ScRad51 and RecA share 30% homology over a span of about 220 amino acids, and each protein contains two conserved ATP binding motifs (Aboussekhra et al., 1992, Mol. and Cell. Biol. 12:3224–34; Basile et al., 1992, Mol. Cell. Biol. 12:3235–46; Sugawara et al., 1995, Nature 373:84–86).

ScRad51 repairs DSB by homologous recombination. DSB accumulate at recombination hot spots during meiosis in cells that lack ScRad51 (Sugawara, 1995), and ScRad51 localizes to meiotic nuclei (Bishop, 1994, Cell 79:1081–92) and promotes meiotic chromosome synapsis (Rockmill et al., 1995, Genes & Develop. 9:2684–95). Accordingly, it is thought that ScRad51 mediates meiotic recombination by binding to single-strands generated at DSB which are in strand pairing and exchange during meiosis (Sung and Robberson, 1995, Cell 82:453–61).

Direct and indirect protein—protein interactions are essential for RecA and ScRad51 function. The crystal structure of RecA suggests that a portion of the N-terminal region is involved in polymer formation (Story et al., 1993, Science 259:1892–96; Story et al., 1992, Nature 355:318–324) which was supported by genetic analysis that showed C-terminal truncations dominantly interfered with DNA repair in wild-type bacteria (Horii et al., 1992, J. Mol. Biol. 223:104–114; Tateishi et al., 1992, J. Mol. Biol. 223:115–129; Yarranton et al., 1982, Mol. Gen. Genet. 185:99–104). A similar self-association region occurs in the N-terminal region of ScRad51 and is essential for DNA repair (Donovan et al., 1994, Genes & Develop. 8:2552–2562; Shinohara et al., 1992, Cell 69:457–70). ScRad51 also associates with Rad52 and Rad55 (Hays et al., 1995, Proc. Natl. Acad. Sci USA 92:6925–6929; Johnson and Symington, 1995, Molec. Cell. Biol. 15(9):4843–4850; Milne and Weaver, 1993, Genes & Develop. 7:1755–1765) as well as other proteins. Other protein interactions may be inferred because a rad51 rad52A strain of *S. cerevisiae* was only partially complemented by Rad51 and Rad52 from *Kluyveromyeces lactis* (Donovan et al., 1994, Genes & Develop. 8:2552–2562), and because ScRad51 colocalized with Dmc1 to the synaptonemal complex (Bishop, 1994, Cell 79:1081–92). These data suggest that a large protein complex is necessary for recombinational repair and that disruption of any of the proteins in this complex hinders the repair of DSB.

RecA/ScRad51 homologues have been discovered in a wide range of organisms including the fission yeast *Schizosaccharomyces pombe* (Jang et al., 1994, Gene 142:207–11; Muris et al., 1993, Nuc. Acids Res. 21:4586–91; Shinohara et al., 1993, Nature Genet. 4:239–4358), lilies (Terasawa et al., 1995, Genes & Develop. 9:925–34), chickens (Bezzubova et al., 1993, Nucl. Acids Res. 21:1577–80), mice (Morita et al., 1993, Proc. Natl. Acad. Sci USA 90:6577–80; Shinohara et al. 1993, Nature Genet. 4:239–43) and humans (Shinohara et al. 1993; Yoshimura et al., 1993, Nucl. Acids Res. 21:1665), and appear to be involved in DNA repair and recombination based on the following evidence: 1) Conserved RecA homology—MmRad51 is 83% homologous, 69% identical to ScRad51, and 51% homologous, 28% identical to RecA. Shared homology between mammalian and yeast Rad51 suggest conserved function due to the remarkable similarity between other mammalian and yeast DNA repair pathways (reviewed in Cleaver, 1994, Cell 76:1–4); 2) Expression pattern—MmRAD51 is highly expressed in tissues involved in meiotic recombination such as testes (Morita et al., 1993, Proc. Natl. Acad. Sci USA 90:6577–80) and ovaries (Shinohara et al., 1993, Nature Genet. 4:239–43). Additionally, expression of the *S. pombe* MmRad51 homologue SpRAD51 increased after cells were treated with methyl methanesulfonate which provides further evidence of a DNA repair function (Jang et al., 1994, Gene 142:207–11); 3) Protein cellular localization—Mouse, chicken, and lily Rad51 localizes at discrete foci on meiotic chromosomes at varying concentrations during prophase 1, possibly on the lateral elements and recombination nodules, which suggests a role in the repair of DSB during meiotic recombination (Ashley et al., 1995, Chromosoma 104:19–28; Haaf et al., 1995, Proc. Natl. Acad. Sci. USA 92:2298–2302; Terasawa et al., 1995). Moreover, increasing concentrations of human Rad51, HsRad51, localize to the nucleus after exposure to DNA damaging agents which also suggests a repair function (Terasawa et al., 1995); 4) Filament formation on DNA—HsRad51 bind to ssDNA which demonstrates a potential for strand exchange (Benson et al., 1994, EMBO 13:5764–71); 5) Mouse cells with a rad51 mutation, designated rad51$^{M1}$, displayed features that are known to be characteristic of unrepaired DSB in yeast cells (Lim and Hasty, 1996, In press) which include reduced proliferation, hypersensitivity to γ-radiation, chromosome loss and programmed cell death.

3.0. SUMMARY OF THE INVENTION

An object of the present invention is to hinder cell proliferation or reduce cell viability by disrupting mammalian Rad51 function.

An additional object is to hinder cell proliferation or reduce cell viability by disrupting mammalian Rad52 function.

Another object of the present invention is to hinder cell proliferation or reduce cell viability by disrupting proteins that associate with mammalian Rad51.

Another object of the present invention is to hinder cell proliferation or reduce cell viability by disrupting proteins that associate with mammalian Rad52.

Another object of the present invention is to hinder cell proliferation or reduce cell viability by disrupting any proteins involved in the mammalian Rad51 or mammalian Rad52 pathways.

Another object of the present invention is to hinder cell proliferation or reduce cell viability by disrupting mammalian Rad$_{51}$ protein interactions.

Another object of the present invention is to hinder cell proliferation or reduce cell viability by disrupting mammalian Rad52 protein interactions.

Another object of the present invention is to hinder cell proliferation or reduce cell viability by disrupting protein—protein interactions that are involved in the mammalian Rad51 or mammalian Rad52 pathways.

Yet another embodiment of the present invention involves methods of identifying compounds that are capable of inhibiting the binding or function of any protein involved in the Rad51 pathway, and, in particular, compounds capable of binding or inhibiting the function of Rad51 protein. Accordingly, an additional embodiment of the present invention involves methods of screening for compounds that disrupt double-stranded break repair by assaying for microsatellite formation in cells; assaying for chromosome loss in cells; assaying for the disruption of strand exchange in an in vitro assay; assaying for decreased cell proliferation; assaying for premature replicative cellular senescence; and assaying for increased cell death.

Another object of the invention is to identify compounds capable of interfering with protein—protein interactions involved in DSB repair by screening large numbers of compounds in assays that allow the detection of a decrease in protein—protein interactions. In a further object of the invention, structural analysis of proteins, peptides, and compounds useful for modulating DSB repair is used to improve the modulation of DSB repair by new or known proteins, peptides, and compounds.

An additional object of the present invention are compounds that hinder cell proliferation or reduce cell viability by disrupting mammalian Rad51 function.

An additional object of the present invention are compounds that hinder cell proliferation or reduce cell viability by disrupting mammalian Rad52 function.

4.0. BRIEF DESCRIPTION OF THE DRAWINGS

FIG. 1. mRNA structure of MmRAD51. The predicted amino acids are numbered according to Shinohara et al., 1993. The shaded box represents the recA homology region. The open boxes represent regions that are not conserved across species. The thick vertical lines represent the ATP binding domains.

Figure 2:
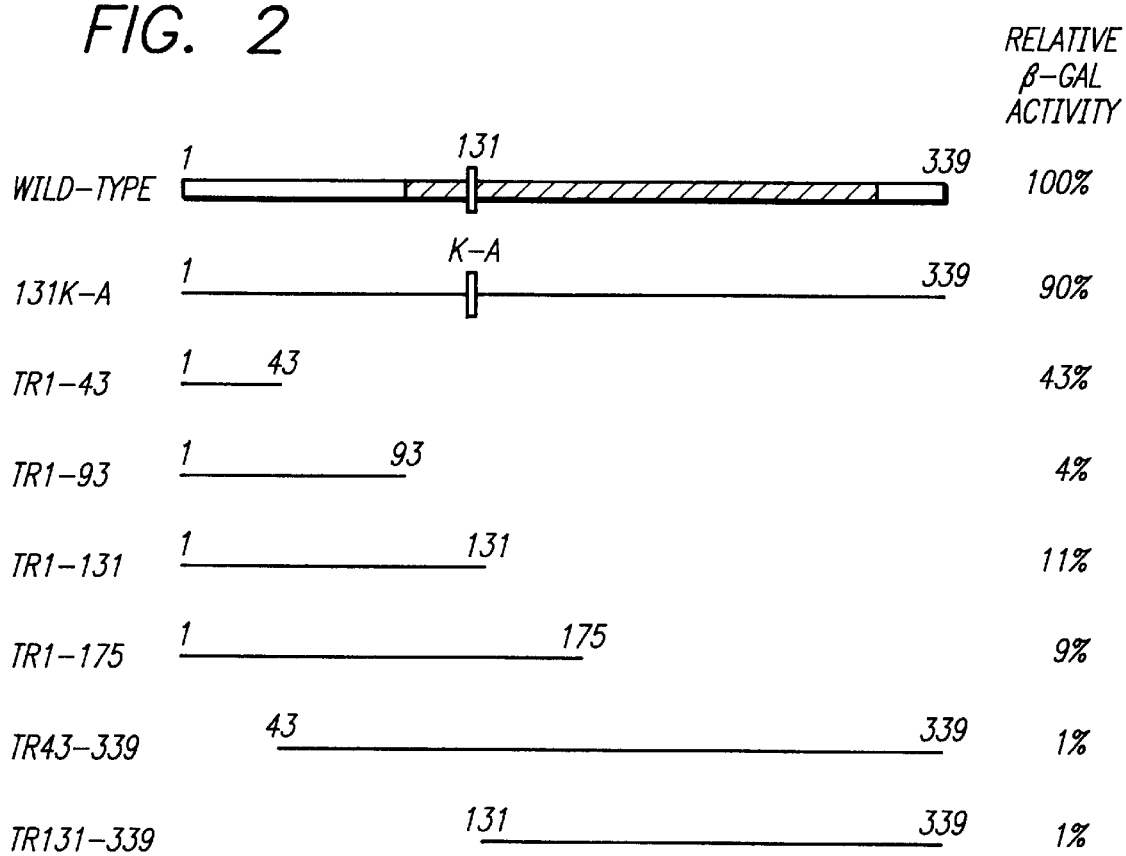

FIG. 2. MmRad51 self-association as demonstrated by the yeast two-hybrid system. The self-association is restricted to the most N-terminal 43 amino acids. The shaded box is the RecA core homology region (Shinohara et al, 1993). The thick vertical lines represent the ATP-binding sites. The open boxes represent regions that are not conserved between species. The relative β-galactosidase (β-gal) activities are presented, right panel. Full length wild-type MmRad51 is considered to be 100%. E12 served as a negative control and had 1% relative activity.

Figure 3:
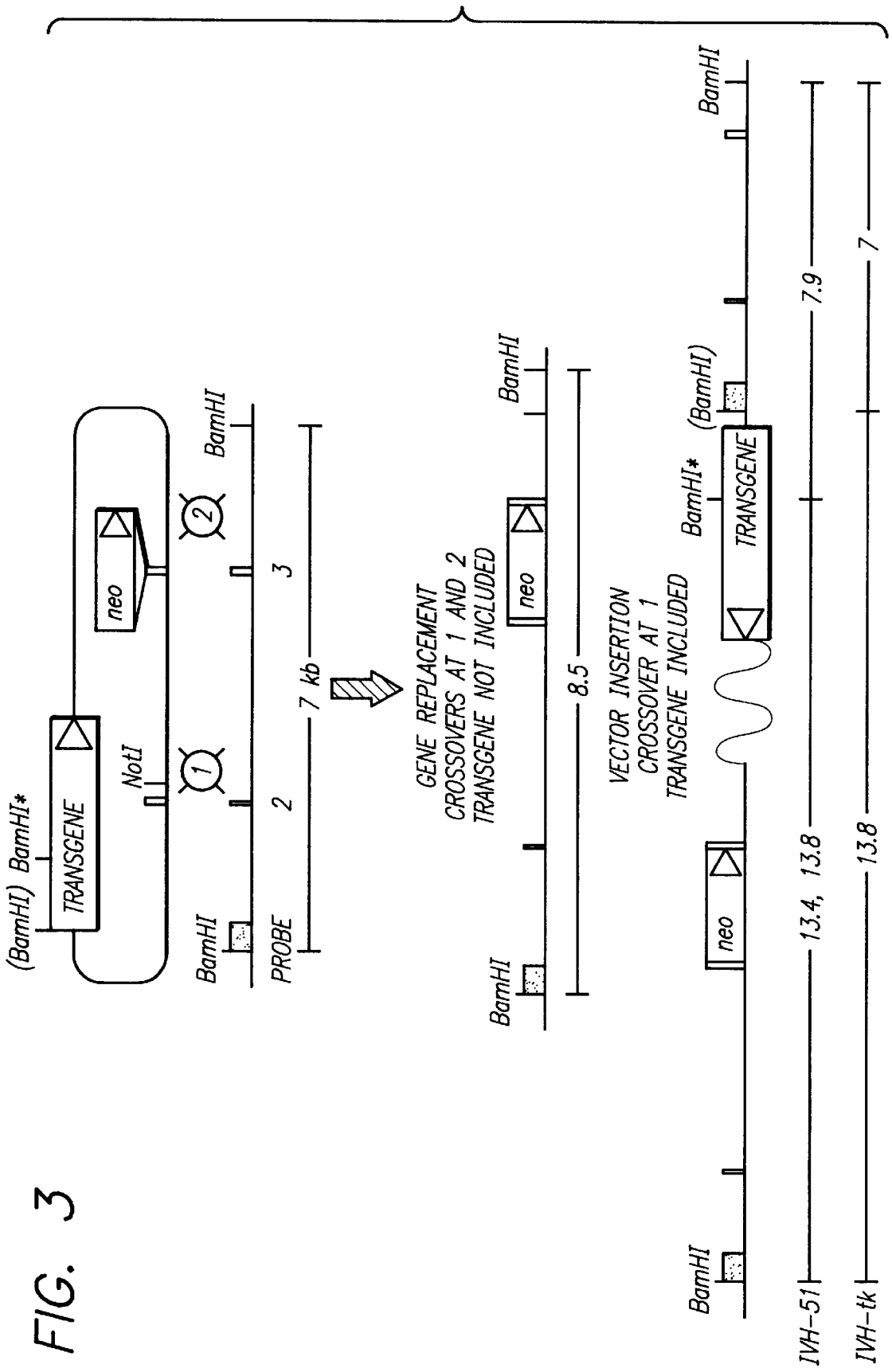

FIG. 3. Targeting the transgenes to the hprt locus. The hprt sequences contain exons 2 and 3 (labeled boxes). Hprt homology of vector origin is a thick line, of chromosomal origin is a thin line. The bacterial plasmid is represented by a wavy line. Potential locations for crossovers are X's labeled 1 or 2. Two recombination events are possible: either gene replacement with crossovers at both 1 and 2 or vector insertion with crossovers at either 1 or 2. For vector insertion, only a crossover at 1 is shown.

Figure 4A:
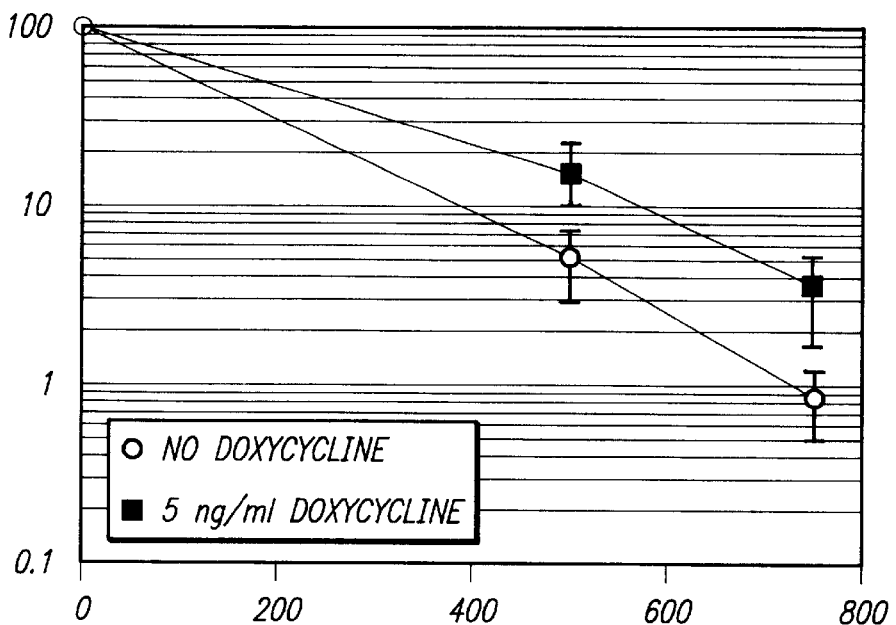
Figure 4B:
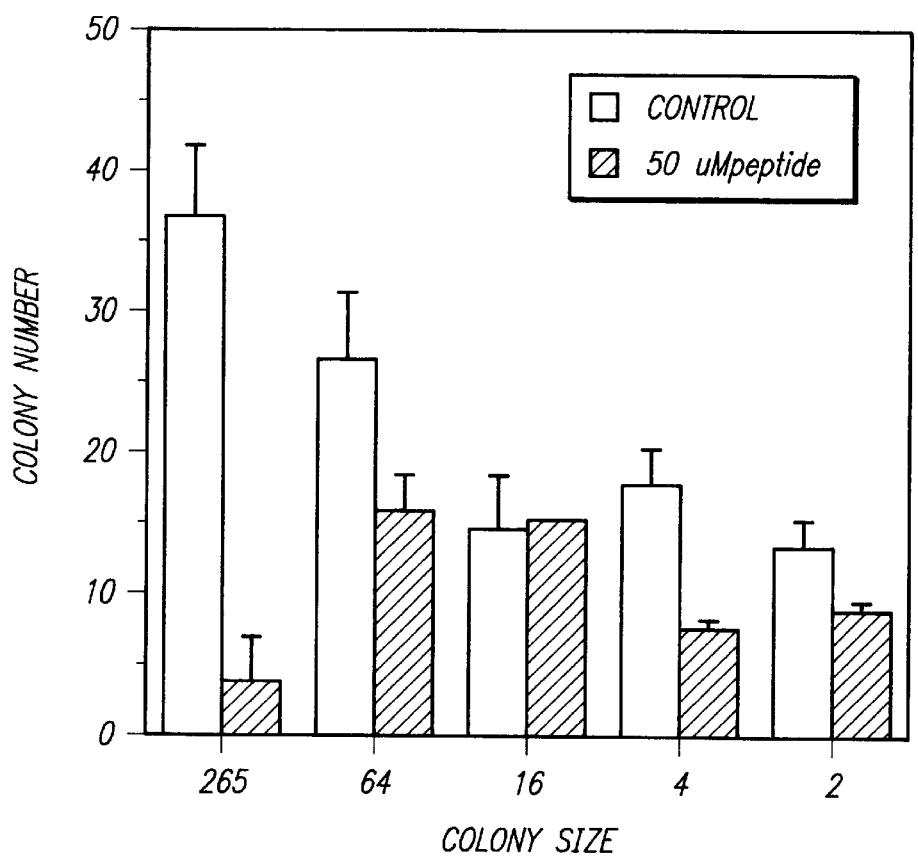

FIGS. 4A and 4B. Disruption of mammalian Rad51 function in cells. A) Conditional expression of mammalian Rad51 1–43 in ES cells increases sensitivity to gamma-radiation. Transgene turned on without Dox and turned off with Dox. Ten clones were observed and the averages are presented. B) Brca2 peptide decreases proliferation of p53—/— fibroblasts. 50 micromolar concentration used. Colony size is based on cell number. The average of two experiments is shown when 100 cells were plated onto a 6 cm plate. The control is either no peptide or the 16 amino acid peptide derived from Antennapedia.

4.0. DETAILED DESCRIPTION OF THE INVENTION

As discussed above, one embodiment of the present invention is the expression of altered mammalian rad51 alleles that disrupt mammalian Rad51 function, mammalian Rad52 function, or the function of any other protein in the mammalian Rad51 or Rad52 pathways. The function of MmRad51 is not entirely known; however, it is likely that it has the same function as ScRad51 which is recombinational repair. The recombinational repair pathway appears to be at least partially conserved between yeast and mammals. Mammalian homologues were found for members of the Rad52 epistasis group (Rad51, Rad52) and to other yeast proteins (Dmc1) implicated in recombinational repair (Malkova et al., 1996, Proc. Natl. Acad. Sci. USA 93:7131–36; Resnick et al., 1989, Proc. Natl. Acad. Sci. USA 86:2276–80; Tsuzuki et al., 1996, Proc. Natl. Acad. Sci USA 93:6236–40). Expression pattern supported the hypothesis that these homologues maintained the same function from yeast to mammals. MmRAD51 was highly expressed in tissues with cells involved in meiotic recombination, testis and ovary, and rapid cell division, intestine, embryo, and thymus (Morita et al., 1993; Shinohara et al., 1993). A role during meiotic recombination was further suggested because MmRAD51 was highly enriched in the synaptonemal complex in pachytene spermatocytes (Ashley et al., 1995; Haaf et al., 1995).

The most compelling evidence that MmRad51 and ScRad51 function is conserved comes from analysis of rad51 mutant cells, the mutation was designated rad51$^{M1}$ (Lim and Hasty, 1996). rad51$^{M1}$ cells exhibited reduced proliferation, hypersensitivity to γ-radiation, chromosome loss and cell death. These characteristics were similar to yeast cells deficient for recombinational repair either due to sequence divergence or due to a mutation in rad51 or rad52. Even though these data suggest MmRad51 functions during recombinational repair it is possible that the severe phenotype in rad51$^{M1}$ cells was due to disruption of another process.

There is evidence that the RecA homologues perform multiple tasks, some of them not shared by the others. Two RecA homologues were found in *Myxococcus xanthus,* only one was essential, but both complemented UV sensitivity in an *E. coli* recA strain (Norioka et al., 1995, J. Bacteriol. 177:4179–82). Two RecA homologues found in yeast, ScRad51 and Dmc1, are essential for meiotic recombination, but only ScRad51 is essential for mitotic recombination (Bishop, 1994, Rockmill et al. 1995, Genes & Develop. 9:2684–95). In mammals, a Dmc1 homologue was isolated suggesting that RecA homologues possess diverse and unique functions in mammalian cells (Habu et al., 1996).

Reduced proliferation, hypersensitivity to γ-radiation, chromosome loss, and cell death have all been associated with rad51$^{M1}$ cells. These characteristics are similar to those seen in yeast cells deficient for recombinational repair either due to sequence divergence, or due to a mutation in rad51 or rad52 (Malkova et al., 1996, Proc. Natl. Acad. Sci. USA 93:7131–36; Resnick et al., 1989, Proc. Natl. Acad. Sci. USA 86:2276–80; Tsuzuki et al., 1996, Proc. Natl. Acad. Sci USA 93:6236–40). Even though these data suggest MmRad51 functions during recombinational repair it is also possible that the severe phenotype observed in rad51$^{M1}$ cells was due to disruption of another process.

For the purposes of the present application the term ionizing radiation shall mean all forms of radiation, including but not limited to a, P, and T radiation and U.V. light, which are capable of directly or indirectly damaging the genetic material of a cell or virus. The term irradiation shall mean the exposure of a sample of interest to ionizing radiation, and the term radiosensitive shall refer to cells or individuals which display unusually adverse consequences after receiving moderate, or medically acceptable (i.e., non-lethal diagnostic or therapeutic doses), exposure to ionizing irradiation.

MmRad51 may perform a novel role in DNA replication, repair, or chromosomal disjunction. MmRAD51 expression is restricted during the cell cycle to late $G_1/S/G_2$ and MmRAD51 expression was activated by mitogens that induced T and B cell proliferation suggesting a role in replication and repair (Yamamoto et al., 1996, 251:1–12). MmRad51 may take part in disjunction because it localizes to the kinetochores of diakinesis, and metaphase 1 chromosomes (Ashley et al., 1995).

The exact function or functions performed by MmRad51 are unimportant with regard to developing anti-proliferative drugs and cancer therapeutics as long as the disruption of the MmRad51 function provides a benefit to the patient. For the purposes of the present invention, it is assumed that the function of Rad51 is the repair of DSB; however, it is likely that Rad51 performs additional functions in the cell. However, it is important to note that at least some aspect of MmRad51 function is essential for cell proliferation and/or viability, and that molecules capable of disrupting MmRad51 function thus hinder cell proliferation or reduce cell viability. As such, any molecule that disrupts the MmRad51 pathway should prove useful for cancer therapy (for example).

Furthermore, disruption of any protein—protein interaction that involves either MmRad51 or any other molecule in the MmRad51 pathway should also prove useful for cancer therapy.

Protein—protein interactions are critical for recombinational repair in yeast cells, including interactions that involve ScRad51 and ScRad52 (Donovan et al., 1994; Milne et al., 1993). In addition, the human Rad51 and Rad52 proteins were shown to associate like their yeast homologues (Shen et al., 1996, J. Biol. Chem. 271:148–152).

To isolate proteins that associate with MmRad51, a yeast two-hybrid screen was performed with MmRad51 as the "bait" and a T cell library and an embryonic cell library as the "prey". Among other proteins identified using this screen, MmRad51 and Brca2 were isolated, and the interactions identified using this screen may prove critical for in vivo function. Additional biochemical binding assays that may prove useful for identifying compounds that are able to associate with MmRad51 (or any other target protein) are well known in the art including, but not limited to: equilibrium or membrane flow dialysis, antibody binding assays, gel-shift assays, in vitro binding assays, filter binding assays, enzyme-linked immunoabsorbent assays (ELISA), western blots, co-immunoprecipitation, immunogold co-immunoprecipitation, coimmunolocalization, co-crystallization, fluorescence energy transfer, competition binding assays, chemical crosslinking, and affinity purification. In addition, genetic analysis may be used to identify accessory proteins that interact with MmRad51 or are peripherally involved in MmRad51 function. Where the MmRad51 accessory protein is essential to MmRad51 function, mutation in the genes encoding these proteins should typically result in phenotypes similar to those associated with MmRad51 mutations. Similarly, where the MmRad51 accessory proteins function to inhibit or retard MmRad51 activity, mutations in the genes encoding these factors shall generally mimic antagonist phenotypes.

The MmRad51 self-association was investigated further. Deletion analysis revealed that the MmRad51 self-association occurred in the N-terminal region which further demonstrated conservation of function with ScRad51 and RecA since both were shown to self-associate via the N-terminal region of the protein (Donovan et al., 1994; Horii, 1992; Story et al., 1992, 1993; Tateishi et al., 1992; Yarranton and Sedgwick, 1982). Although the presently described invention has been specifically exemplified using a species exemplary of the order mammalia, given the relatively high level of interspecies sequence similarity (and functional similarity) observed in the Rad51 proteins, it is clear that the present invention may be broadly applied to other mammalian species, including humans, as well as non-mammalian animals such as birds, and fish.

In addition to mice, examples of mammalian species that may be used in the practice of the present invention include, but are not limited to: humans, non-human primates (such as chimpanzees), pigs, rats (or other rodents), rabbits, cattle, goats, sheep, and guinea pigs.

Given the critical importance of mammalian Rad51 function, any disruption of the mammalian Rad51 or Rad52 complexes, or any member in their pathway will necessarily hinder cell proliferation or viability. When the Rad51 and Rad52 pathways were disrupted by introducing altered mouse rad51 into mouse cells, nonproductive protein—protein associations resulted. The altered forms of mouse rad51 were generated by disrupting a conserved nucleotide binding motif while preserving the protein association domain. The expression of these transgenes resulted in cellular toxicity. Presumably, the resulting nonproductive protein associations were responsible for the drastically reduced viability of these cells. In view of this result, it is clear one may reduce cell proliferation by disrupting mammalian Rad51 function, or the function of any protein in this repair pathway by hindering protein association by using defective proteins or other means such as small molecules.

Given that the Rad51 proteins are known to self-associate, the Rad51 protein sequence provides a template for the identification and genesis of peptides or factors that disrupt Rad51 function or activity For the purposes of the present invention a "peptide" is any sequence of at least about five amino acids up to about 100 amino acids. Typically, the peptides of the present invention can encompass enzymatic domains, DNA, RNA, or protein binding domains, or any fragment of a protein or amino acid sequence that directly or indirectly provide the desired function of disrupting cellular Rad51 or Rad52 activity. Accordingly, an additional embodiment of the present invention are peptides or polypeptides that correspond at least five contiguous amino acids of the mammalian Rad51 amino acid sequence (SEQ ID NO. 1), or the human Rad51 amino acid sequence (SEQ ID NO. 2) that retain the property of being capable of binding a mammalian Rad51 and/or inhibiting Rad51 function (as detected using a suitable biochemical, genetic, or cellular assay).

Additionally, the blocking of normal Rad51 function may induce programmed cell death. Thus, one aspect of the present invention are a novel class of therapeutic agents, factors, or compounds that have been engineered, or are otherwise capable of disrupting the essential processes that are mediated by, or associated with, normal Rad51 or Rad52 activity. Accordingly, it is contemplated that this novel class of therapeutics agents may be used to treat diseases including, but not limited to, autoimmune disorders and diseases, inflammation, cancer, graft rejection, and any of a variety of proliferative or hyperproliferative disorders.

Typical examples of therapeutic agents based on the above presently described molecules include, but are not limited to, defective (either engineered or naturally occurring) forms of the proteins that associate with the protein complexes, inhibitory fragments of the proteins, wild type and altered genes that code for proteins that disrupt mammalian Rad51 function, small organic molecules, anti-sense nucleic acid sequences, oligonucleotides that inhibit expression or activity via a triplex mechanism, peptides, aptameric oligonucleotides, and the like.

More particularly, examples of engineered proteins may include, but are not limited to, proteins that comprise inactivating mutations in conserved active sites (e.g., ATP binding motifs, DNA or protein binding domains, catalytic sites, etc.), fusion proteins that comprise at least one inhibitory domain, and the like.

The above agents may be obtained from a wide variety of sources. For example, standard methods of organic synthesis may be used to generate small organic molecules that mimic the desired regions of the target DNA repair proteins. In addition, combinatorial libraries comprising a vast number of compounds (organic, peptide, or nucleic acid, reviewed in Gallop et al. 1994, J. Med. Chem. 37(9):1233–1251; Gordon et al., 1994, J. Med. Chem. 37(10):1385–1401; and U.S. Pat. No. 5,424,186 all of which are herein incorporated by reference) may be screened for the ability to bind and inhibit the activity of proteins involved in DSB repair or any other potential mammalian Rad51 function.

In particular, inhibitory peptides should prove very useful. Such compounds may include, but are not limited to, peptides such as, for example, soluble peptides, including but not limited to members of random peptide libraries; (see, e.g., Lam et al., 1991, Nature 354:82–84; Houghten et al., 1991, Nature 354:84–86), and combinatorial chemistry-derived molecular library made of D- and/or L- configuration amino acids, phosphopeptides (including, but not limited to members of random or partially degenerate, directed phosphopeptide libraries; see, e.g., Songyang et al., 1993, Cell 72:767–778).

Given that an important aspect of DSB repair is the interaction of proteins, additional aspects of the invention are the use of screening assays to detect interactions or the lack of such interactions of proteins involved in DSB repair. The following assays are designed to identify compounds that interact with (e.g., bind to) proteins involved in DSB repair. The compounds which may be screened in accordance with the invention include but are not limited to peptides, antibodies and fragments thereof, prostaglandins, lipids and other organic compounds (e.g., terpines, peptidomimetics) that bind to or mimic the activity triggered by a natural ligand (i.e., agonists) or inhibit the activity triggered by a natural ligand (i.e., antagonists) of a protein involved in DSB repair; as well as peptides, antibodies or fragments thereof, and other organic compounds that mimic the natural ligand for a given protein involved in DSB repair.

Such compounds may include, but are not limited to, peptides such as, for example, soluble peptides, including but not limited to members of random peptide libraries (see, e.g., Lam, K. S. et al., 1991, *Nature,* 354:82–84; Houghten, R. et al., 1991, *Nature,* 354:84–86), and combinatorial chemistry-derived molecular library peptides made of D- and/or L- configuration amino acids, phosphopeptides (including, but not limited to members of random or partially degenerate, directed phosphopeptide libraries; see, e.g., Songyang, Z. et al., 1993, *Cell,* 72:767–778); antibodies (including, but not limited to, polyclonal, monoclonal, humanized, anti-idiotypic, chimeric or single chain =antibodies, and FAb, F(ab)$_2$ and FAb expression library fragments, and epitope-binding fragments thereof); and small organic or inorganic molecules.

Other compounds which can be screened in accordance with the invention include but are not limited to small organic molecules that are able to gain entry into an appropriate cell and affect DSB repair by, for example, modulating protein—protein interactions important for DSB repair (e.g., by interacting with a protein involved in DSB repair); or such compounds that affect the activity of a gene encoding a protein involved in DSB repair.

Computer modeling and searching technologies permit identification of compounds, or the improvement of already identified compounds, that can modulate DSB repair by, for example, modulating protein—protein interactions involved in DSB repair. Having identified such a compound or composition, the active sites or regions are identified. Such active sites might typically be the binding partner sites, such as, for example, the interaction domains of a protein important for DSB repair with its cognate ligand. The active site can be identified using methods known in the art including, for example, from the amino acid sequences of peptides, from the nucleotide sequences of nucleic acids, or from study of complexes of the relevant compound or composition with its natural ligand. In the latter case, chemical or X-ray crystallographic methods can be used to find the active site by finding where on the factor the complexed ligand is found.

Next, the three dimensional geometric structure of the active site is determined. This can be done by known methods, including X-ray crystallography, which can determine a complete molecular structure. On the other hand, solid or liquid phase NMR can be used to determine certain intra-molecular distances. Any other experimental method of structure determination can be used to obtain partial or complete geometric structures. The geometric structures may be measured with a complexed ligand, natural or artificial, which may increase the accuracy of the active site structure determined.

If an incomplete or insufficiently accurate structure is determined, the methods of computer based numerical modeling can be used to complete the structure or improve its accuracy. Any recognized modeling method may be used, including parameterized models specific to particular biopolymers such as proteins or nucleic acids, molecular dynamics models based on computing molecular motions, statistical mechanics models based on thermal ensembles, or combined models. For most types of models, standard molecular force fields, representing the forces between constituent atoms and groups, are necessary, and can be selected from force fields known in physical chemistry. The incomplete or less accurate experimental structures can serve as constraints on the complete and more accurate structures computed by these modeling methods.

Finally, having determined the structure of the active site, either experimentally, by modeling, or by a combination thereof, candidate modulating compounds can be identified by searching databases containing compounds along with information on their molecular structure. Such a search seeks compounds having structures that match the determined active site structure and that interact with the groups defining the active site. Such a search can be manual, but is preferably computer assisted. The compounds found from such a search generally identify modulating compounds, or genes encoding the same, that are selected for further study or gene targeting.

Alternatively, these methods can be used to identify improved modulating compounds from an already known modulating compound or ligand. The composition of the known compound can be modified and the structural effects of modification can be determined using the experimental and computer modeling methods described above applied to the new composition. The altered structure is then compared to the active site structure of the compound to determine if an improved fit or interaction results. In this manner systematic variations in composition, such as by varying side groups, can be quickly evaluated to obtain modified modulating compounds or ligands of improved specificity or activity.

Further experimental and computer modeling methods useful to identify modulating compounds based upon identification of the active sites of regulatory protein interactions, and related transduction factors will be apparent to those of skill in the art.

Representative examples of molecular modeling systems include the CHARMm and QUANTA programs (Polygen Corporation, Waltham, Mass.). CHARMm performs the energy minimization and molecular dynamics functions. QUANTA performs the construction, graphic modeling and analysis of molecular structure. QUANTA allows interactive construction, modification, visualization, and analysis of the behavior of molecules with each other.

Although described above with reference to design and generation of compounds which could alter binding, one could also screen libraries of known compounds, including natural products or synthetic chemicals, and biologically active materials, including proteins, for compounds which are inhibitors or activators of the proteins and genes that are important for any aspect of DSB repair.

In vitro systems may be designed to identify compounds capable of interacting with (e.g., binding to) the regulatory proteins identified using the subject methods. The identified compounds may be useful, for example, in modulating the activity of wild type and/or mutant proteins important for DSB repair. In vitro systems may also be utilized to screen for compounds that disrupt normal interactions important for DSB repair.

The assays used to identify compounds that bind to proteins important for DSB repair involve preparing a reaction mixture of a given protein and the test compound under conditions and for a time sufficient to allow the two components to interact and bind, thus forming a complex which can be removed and/or detected in the reaction mixture. The protein used can vary depending upon the goal of the screening assay. For example, where agonists of the natural ligand are sought, a full length protein, or a fusion protein containing a protein or polypeptide that affords advantages in the assay system (e.g., labeling, isolation of the resulting complex, etc.) can be utilized.

The screening assays can be conducted in a variety of ways. For example, one method to conduct such an assay would involve anchoring the protein, polypeptide, peptide or fusion protein or the test substance onto a solid phase and detecting binding between the protein and test compound. In one embodiment of such a method, the protein reactant may be anchored onto a solid surface, and the test compound, which is not anchored, may be labeled, either directly or indirectly. In another embodiment of the method, the test protein is anchored on the solid phase and is complexed with a labeled antibody (and where a monoclonal antibody is used, it is preferably specific for a given region of the protein). Then, a test compound could be assayed for its ability to disrupt the association of the protein/antibody complex.

In practice, microtiter plates, or any modernized iteration thereof, may conveniently be utilized as the solid phase. The anchored component may be immobilized by non-covalent or covalent attachments. Non-covalent attachment may be accomplished by simply coating the solid surface with a solution of the protein and drying. Alternatively, an immobilized antibody, preferably a monoclonal antibody, specific for the protein to be immobilized may be used to anchor the protein to the solid surface. The surfaces may be prepared in advance and stored.

In order to conduct the assay, the nonimmobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously nonimmobilized component is pre-labeled, the detection of label immobilized on the surface indicates that complexes were formed. Where the previously nonimmobilized component is not pre-labeled, an indirect label can be used to detect complexes anchored on the surface; e.g., using a labeled antibody specific for the previously nonimmobilized component (the antibody, in turn, may be directly labeled or indirectly labeled with a labeled anti-Ig antibody).

Alternatively, a reaction can be conducted in a liquid phase, the reaction products separated from unreacted components, and complexes detected; e.g., using an immobilized antibody specific for the test protein, polypeptide, peptide or fusion protein, or the test compound to anchor any complexes formed in solution, and a labeled antibody specific for the other component of the possible complex to detect anchored complexes.

Macromolecules that interact with a given protein important for DSB repair are referred to, for purposes of this discussion, as "binding partners". Therefore, it is desirable to identify compounds that interfere with or disrupt the interaction with such binding partners which may be useful in modulating DSB repair.

The basic principle of the assay systems used to identify compounds that interfere with the interaction between a protein and its binding partner or partners involves preparing a reaction mixture containing the test protein, polypeptide, peptide or fusion protein as described above, and the binding partner under conditions and for a time sufficient to allow the two to interact and bind, thus forming a complex. In order to test a compound for inhibitory activity, the reaction mixture is prepared in the presence and absence of the test compound. The test compound may be initially included in the reaction mixture, or may be added at a time subsequent to the addition of the test protein and its binding partner. Control reaction mixtures are incubated without the test compound or with a placebo.

The formation of any complexes between the test protein and the binding partner is then detected. The formation of a complex in the control reaction, but not in the reaction mixture containing the test compound, indicates that the compound interferes with the interaction of the test protein and the binding partner.

The assay for compounds that interfere with protein binding can be conducted in a heterogeneous or homogeneous format. Heterogeneous assays involve anchoring either the test protein or the binding partner onto a solid phase and detecting complexes anchored on the solid phase at the end of the reaction. In homogeneous assays, the entire reaction is carried out in a liquid phase. The examples below describe similar assays which may be easily modified to screen for compounds which disrupt or enhance the interaction. In either approach, the order of addition of reactants can be varied to obtain different information about the compounds being tested. For example, test compounds that interfere with the interaction by competition can be identified by conducting the reaction in the presence of the test substance; i.e., by adding the test substance to the reaction mixture prior to or simultaneously with the test protein and interactive binding partner. Alternatively, test compounds that disrupt preformed complexes, e.g., compounds with higher binding constants that displace one of the components from the complex, can be tested by adding the test compound to the reaction mixture after complexes have been formed. The various formats are described briefly below.

In a heterogeneous assay system, either the test protein, or the interactive binding partner, is anchored onto a solid surface, while the non-anchored species is labeled, either directly or indirectly. In practice, microtiter plates are conveniently utilized. The anchored species may be immobilized by non-covalent or covalent attachments. Non-covalent attachment may be accomplished simply by coating the solid surface with a solution of the test protein or binding partner and drying. Alternatively, an immobilized antibody specific for the species to be anchored may be used to anchor the species to the solid surface. The surfaces may be prepared in advance and stored.

In order to conduct the assay, the partner of the immobilized species is exposed to the coated surface with or without the test compound. After the reaction is complete, unreacted components are removed (e.g., by washing) and any complexes formed will remain immobilized on the solid surface. The detection of complexes anchored on the solid surface can be accomplished in a number of ways. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, may be directly labeled or indirectly labeled with a labeled anti-Ig antibody). Depending upon the order of addition of reaction components, test compounds which inhibit complex formation or which disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds which inhibit complex or which disrupt preformed complexes can be identified.

In an alternate embodiment of the invention, a homogeneous assay can be used. In this approach, a preformed complex of the test protein and the interactive binding partner is prepared in which either protein is labeled, but the signal generated by the label is quenched due to formation of the complex (see, e.g., U.S. Pat. No. 4,109,496 by Rubenstein which utilizes this approach for immunoassays). The addition of a test substance that competes with and displaces one of the species from the preformed complex will result in the generation of a signal above background. In this way, test substances which disrupt the binding interaction can be identified.

For an example of a typical labeling procedure, a test protein or a peptide fragment, e.g., corresponding to the relevant binding domain, can be fused to a glutathione-S-transferase (GST) gene using a fusion vector, such as pGEX-5X-1, in such a manner that its binding activity is maintained in the resulting fusion protein. The interactive binding partner can be labeled with radioactive isotope, for example, by methods routinely practiced in the art. In a heterogeneous assay, e.g., the GST-fusion protein can be anchored to glutathione-agarose beads. The interactive binding partner can then be added in the presence or absence of the test compound in a manner that allows interaction and binding to occur. At the end of the reaction period, unbound material can be washed away. The interaction between the fusion product and the labeled interactive binding partner can be detected by measuring the amount of radioactivity that remains associated with the glutathione-agarose beads. The successful inhibition of binding by the test compound will result in a decrease in measured radioactivity.

Alternatively, the GST-fusion protein and the labeled interactive binding partner can be mixed together in liquid in the absence of the solid glutathione-agarose beads. The test compound can be added either during or after the species are allowed to interact. This mixture can then be added to the glutathione-agarose beads and unbound material is washed away. Again the extent of binding inhibition can be measured by determining the amount of radioactivity associated with the beads.

In another embodiment of the invention, these same techniques can be employed using peptide fragments that correspond to the binding domains of the test proteins, in place of the full length proteins. Any number of methods routinely practiced in the art can be used to identify and isolate the binding sites. These methods include, but are not limited to, mutagenesis of the gene encoding the protein and screening for disruption of binding in a co-immunoprecipitation assay. Sequence analysis of the gene encoding the protein will reveal the mutations that correspond to the region of the protein involved in interactive binding.

The invention encompasses cell-based and animal model-based assays for the identification of compounds exhibiting the ability to alter or correct phenotypes associated with the various genotypes identified and constructed using the present methods. Such cell-based assays can also be used as the standard to assay for purity and potency of the compounds, including recombinantly or synthetically produced proteins or compounds.

Given that they will serve as templates for the rational design of agents for disrupting DSB repair activity in the cell, it would be advantageous to purify each of the individual proteins that are directly or indirectly involved in DSB repair of any other potential mammalian Rad51 function. The various proteins involved in the DSB repair pathways may be purified using any of a number of variations of well established biochemical, and molecular biology techniques. Such techniques are well known to those of ordinary skill in the biochemical arts and have been extensively described in references such as Berger and Kimmel, *Guide to Molecular Cloning Techniques, Methods in Enzymology*, Volume 152, Academic Press, San Diego, Calif. (1987; *Molecular Cloning: A Laboratory Manual*, 2d ed., Sambrook, J., Fritsch, E. F., and Maniatis, T. (1989); *Current Protocols in Molecular Biology*, John Wiley & Sons, all Vols., 1989, and periodic updates thereof); *New Protein Techniques: Methods in Molecular Biology*, Walker, J. M., ed., Humana Press, Clifton, N.J., 1988; and *Protein Purification: Principles and Practice*, 3rd. Ed., Scopes, R. K., Springer-Verlag, New York, N.Y., 1987. In general, techniques including, but not limited to, ammonium sulfate precipitation; centrifugation, ion exchange, gel filtration, and reverse-phase chromatography (and the HPLC or FPLC forms thereof) may be used to purify the various proteins of the DSB repair complex.

Additionally, purified preparations of the presently described DNA repair proteins, associated proteins, or fragments thereof, may be used to generate antisera specific for a given agent. Accordingly, additional embodiments of the present invention include polyclonal and monoclonal antibodies that recognize epitopes of the presently described DNA repair complex proteins. The factors used to induce the antibodies of interest need not be biologically active; however, the factors should induce immunological activity in the animal used to generate the antibodies.

Given that similar methodologies may be applied to the generation of antibodies to the various factors, for purposes of convenience, only the Rad51 factor antibodies will be discussed further.

Polypeptides for use in the induction of Rad51-specific antibodies may have an amino acid sequence consisting of at least three amino acids, and preferably at least 10 amino acids, that mimic a portion of the amino acid sequence of Rad51, and may contain the entire amino acid sequence of naturally occurring Rad51 or a Rad51-derivative.

Anti-Rad51 antibodies are expected to have a variety of medically useful applications, several of which are described generally below. More detailed and specific descriptions of various uses for anti-Rad51 antibodies are provided in the sections and subsections which follow. Briefly, anti-Rad51 antibodies may be used for the detection and quantification of Rad51 polypeptide expression in cultured cells, tissue samples, and in vivo. Such immunological detection of Rad51 may be used, for example, to identify, monitor, and assist in the prognosis of neoplasms that have been treated with factors that inhibit DSB repair. Additionally, monoclonal antibodies recognizing epitopes from different parts of the Rad51 structure may be used to detect and/or distinguish between native Rad51 and various subcomponent and/or mutant forms of the molecule. Additionally, anti-Rad51 monoclonal antibodies may be used to test preparations of agents or factors that mimic segments of Rad51, or are designed to impair protein association with Rad51, or to competitively inhibit DNA binding. In addition to the various diagnostic and therapeutic utilities of anti-Rad51 antibodies, a number of industrial and research applications will be obvious to those skilled in the art, including, for example, the use of anti-Rad51 antibodies as affinity reagents for the isolation of Rad51-associated polypeptides, and as immunological probes for elucidating the biosynthesis, metabolism and biological functions of Rad51. Rad51 antibodies may also be used to purify Rad51 or Rad51-associated factors by affinity chromatography.

Once purified, the proteins of interest may be partially sequenced, and these data may be used to design degenerate oligonucleotide probes for use in cloning the genes encoding the various proteins that are associated with DSB repair. Alternatively, any of a variety of public or private sequence data bases may be searched for nucleic acid or peptide sequences that share homology with genes and proteins associated with Rad51-mediated DSB repair. Once a similar sequence is identified, peptides may be produced and screened for inhibitory activity. Where a nucleic acid library is involved, one could synthesize a probe corresponding to the nucleic acid sequence of interest, and use the probe to clone a full-length version of the corresponding gene (if necessary). Accordingly, an additional embodiment of the presently claimed invention are nucleic acid sequences that are capable of hybridizing to sequences encoding the proteins that are associated with DSB repair under stringent conditions. For the purposes of the present invention, the term "stringent conditions" generally refers to hybridization conditions that (1) employ low ionic strength and high temperature for washing, for example, 0.015 M NaCl/0.0015 M sodium citrate/0.1% SDS at 50° C.; or (2) employ during hybridization a denaturing agent such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C.; or (3) employ 50 formamide, 5× SSC (0.75 M NaCl, 0.075 M Sodium pyrophosphate, 5× Denhardt's solution, sonicated salmon sperm DNA (50 g/ml), 0.1% SDS, and 10% dextran sulfate at 42° C., with washes at 42° C. in 0.2× SSC and 0.1% SDS. The above examples of hybridization conditions are merely provided for purposes of exemplification and not limitation. A more thorough treatise of the such routine molecular biology techniques may be found in Sambrook et al., *Molecular Cloning,* Cold Spring Harbor Laboratory Press, Cold Spring Harbor, New York, Vols. 1–3: (1989), and periodic updates thereof, herein incorporated by reference.

Once isolated, the genes encoding the proteins involved in DSB repair may be recombinantly expressed using standard vectors and hosts. Examples of vectors that may be used to express proteins of interest are provided in Sambrook et al., *Molecular Cloning,* Cold Spring Harbor Laboratory Press, Cold Spring Harbor, New York, Vols. 1–3: (1989). In particular, eucaryotic viruses may be used as vectors to transduce any of a wide variety of plant and animal cells to overexpress the desired proteins. Examples of such viruses include, but are not limited to, adenovirus, papilloma virus, herpes virus, adeno-associated virus, rabies virus, bacculo virus, retrovirus, plant viruses, and the like (See generally, Sambrook et al., *Molecular Cloning,* Cold Spring Harbor Laboratory Press, Cold Spring Harbor, New York, Vol. 3:16.1–16.89 (1989); U.S. Pat. No. 5,316,931, issued May 31, 1994, herein incorporated by reference).

Preferably, agents that disrupt DSB repair shall be substantially specific for blocking the desired repair pathways. For the purposes of the present invention, the term substantially specific shall mean that a given agent is capable of being dosaged to provide the desired effect while not causing undue cellular toxicity.

One of ordinary skill will appreciate that, from a medical practitioner's or patient's perspective, virtually any alleviation or prevention of an undesirable symptom (e.g., symptoms related to disease, sensitivity to environmental factors, normal aging, and the like) would be desirable. Thus, for the purposes of this Application, the terms "treatment", "therapeutic use", or "medicinal use", used herein shall refer to any and all uses of compositions comprising the claimed agents which remedy a disease state or symptoms, or otherwise prevent, hinder, retard, or reverse the progression of disease or other undesirable symptoms in any way whatsoever.

When used in the therapeutic treatment of disease, an appropriate dosage of presently described agents, or derivatives thereof, may be determined by any of several well established methodologies. For instance, animal studies are commonly used to determine the maximal tolerable dose, or MTD, of bioactive agent per kilogram weight. In general, at least one of the animal species tested is mammalian. Those skilled in the art regularly extrapolate doses for efficacy and avoiding toxicity to other species, including human. Before human studies of efficacy are undertaken, Phase I clinical studies in normal subjects help establish safe doses.

Additionally, the bioactive agents may be complexed with a variety of well established compounds or structures that, for instance, enhance the stability of the bioactive agent, or otherwise enhance its pharmacological properties (e.g., increase in vivo half-life, reduce toxicity, etc.).

Another aspect of the present invention includes formulations that provide for the sustained release of DSB repair antagonists. Examples of such sustained release formulations include composites of biocompatible polymers, such as poly(lactic acid), poly(lactic-co-glycolic acid), methylcellulose, hyaluronic acid, collagen, and the like. The structure, selection and use of degradable polymers in drug delivery vehicles have been reviewed in several publications, including, A. Domb et al., *Polymers for Advanced Technologies* 3:279–292 (1992). Additional guidance in selecting and using polymers in pharmaceutical formulations can be found in the text by M. Chasin and R. Langer (eds.), "Biodegradable Polymers as Drug Delivery Systems, " Vol. 45 of "Drugs and the Pharmaceutical Sciences," M. Dekker, New York, 1990. Liposomes may also be used to provide for the sustained release of DSB repair antagonists. Details concerning how to use and make liposomal formulations of drugs of interest can be found in, among other places, U.S. Pat. No 4,944,948; U.S. Pat. No. 5,008,050; U.S. Pat. No. 4,921,706; U.S. Pat. No. 4,927,637; U.S. Pat. No. 4,452,747; U.S. Pat. No. 4,016,100; U.S. Pat. No. 4,311,712; U.S. Pat. No. 4,370,349; U.S. Pat. No. 4,372,949; U.S. Pat. No. 4,529,561; U.S. Pat. No. 5,009,956; U.S. Pat. No. 4,725,442; U.S. Pat. No. 4,737,323; U.S. Pat. No. 4,920,016. Sustained release formulations are of particular interest when it is desirable to provide a high local concentration of DSB repair antagonist, e.g., near a tumor, site of inflammation, etc.

Where diagnostic, therapeutic or medicinal use of the presently described agents, or derivatives thereof, is contemplated, the bioactive agents may be introduced in vivo by any of a number of established methods. For instance, the agent may be administered by inhalation; by subcutaneous (sub-q); intravenous (I.V.), intraperitoneal (I.P.), or intramuscular (I.M.) injection; or as a topically applied agent (transdermal patch, ointments, creams, salves, eye drops, and the like).

Additionally, an alternative means for employing the presently disclosed anti-proliferation agents includes the use of vectors to directly insert genes encoding the agents into target cells (e.g., gene therapy). For example, when the tumor cells express the genes encoding the desired sequences, DSB repair will be disrupted and the tumor cell will die. Alternatively, one could attack tumor cells using a strategy conceptually similar to that disclosed in U.S. Pat. No. 5,529,774 herein incorporated by reference. In brief, cells that produce transducing virus encoding sequence that disrupts DSB repair may be implanted at or near the tumor mass. As the producer cells continue to elaborate virus, the growing tumor cells are infected and effectively killed as they express the agent that blocks DSB repair. The above methodology has proven useful in the treatment of glioblastomas and other tumors of the brain by using retroviral vectors to selectively target actively replicating tumor cells. A similar methodology could be used to deliver antisense sequences that target (and thus inhibit) the expression of Rad51 or any of the proteins involved in the Rad51 or Rad52 pathways.

The mammalian $Rad_{51}$ or Rad52-mediated repair pathways, and the associated proteins, are essential for cell proliferation or viability. These DNA repair pathways most likely function by repairing DSB via homologous recombination between sister chromatids during $S/G_2$ (recombinational repair); however, during $G_1$, the repair of DSB may also occur via nonhomologous recombination (nonhomologous end joining). The nonhomologous recombination pathway was once thought to be the major repair pathway in mammalian cells. Much of this belief stems from gene targeting data that demonstrated homologous recombination to be less frequent than random or illegitimate recombination (Bradley et al., 1992, Bio/Technology 10:534–39). Other data demonstrated that chromosomal DSB frequently were joined without homology or with only very short stretches of homology (Rouet and Jasin, 1994, Mol. Cell. Biol. 14:8096–8105). DNA-dependent protein kinase (DNA-PK) is critical for nonhomologous but not homologous repair of DSB (Liang et al., 1996, Proc. Natl. Acad. Sci. USA 93:8929–33). A biphasic response to ionizing radiation was observed in DNA-PK-deficient cell lines with resistance in late S phase suggesting that DNA-PK functions in $G_1$ and another repair pathway functions in S phase (Jeggo, 1990, Mutation Research 239:1–16). DNA-PK is composed of a catalytic subunit called DNA-$PK_{cs}$ and a DNA end-binding subunit called Ku which is a heterodimer of Ku70 and Ku86 (Park et al., 1996, J. Biol. Chem. 1996:18996–19000, for review, see Roth et al., 1995; Shen et al., 1996. Analysis 30 of DNA-PK activity has come from scid (severe combined immunodeficient) mice which are deficient in DNA-$PK_{cs}$ (Kirchgessner et al., 1995, Science 267:1178–82), and Ku86-deficient mice (Nussenzweig et al., 1996, Nature 382:551–55; Zhu et al., 1996, Cell 86:379–89). Both scid and Ku86-deficient mice are immune deficient due to a defect in repair of DSB generated during V(D)J recombination. Unfortunately, it is impossible to analyze V(D)J recombination in rad51-mutant mice or cells; however, it is unlikely that MmRad51 plays a role in this process since MmRad51 localizes to the nucleus in late $G_1$ through $G_2$ (Yamamoto et al., 1996, 251:1–12), and V(D)J recombination occurs in $G_0/G_1$ (Schlissel et al., 1993, Genes & Dev. 7:2520–32). In general, scid and Ku86-deficient cells do have similarities to MmRad51-deficient cells. All are hypersensitive to ionizing radiation, and Ku86-deficient cells were prematurely senescent in tissue culture, indicating a similar function. However, since scid and Ku86-deficient mice and cells were viable and MmRad51-deficient cells were not, the consequences of removing the putative homologous recombination pathway to repair DSB appears to be more vital than the removal of the nonhomologous pathway.

The presently described DSB repair antagonists are particularly deemed useful for the treatment of cancer. Cancers that may be treated by the methods of the invention include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastom, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tutrr, chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiforme, oligodendroglioma, schwannoma, retinoblastoma, congenital tumors), spinal cord (neurofibroma, meningioma, glioma, sarcoma); Gynecological: uterus (endometrial carcinoma), cervix (cervical carcinoma, pre-tumor cervical dysplasia), ovaries (ovarian carcinoma, [serous cystadenocarcinoma, mucinous cystadenocarcinoma, endometrioid tumors, celioblastoma, clear cell carcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma [embryonal rhabdomyosarcoma], fallopian tubes (carcinoma); Hematoloqic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles, dysplastic nevi, lipoma, angioma, dermatofibroma, keloids, psoriasis; and Adrenal glands: neuroblastoma.

In addition to cancer, the presently disclosed compounds are effective against any of a wide variety of hyperproliferative disorders including, but not limited to: autoimmune disease, arthritis, inflammatory bowel disease, proliferation induced after medical procedures, including, but not limited to, surgery, angioplasty, and the like.

The anti-cancer application of agents that functionally disrupt mammalian Rad51, Rad52 or any member in the DSB repair pathway, requires that DSB repair remains equally critical in cancer cells. Cancer cells lack many of the normal cell cycle regulatory mechanisms that are critical to controlling proliferation, and inducing programmed cell death, and it remains possible that the absence of these mechanisms renders Rad51 and/or Rad52 function nonessential. The protein p53 is central to regulation of the cell cycle, and stimulation of cell death in response to DNA damage including DNA damaged by ionizing radiation (reviewed by Ko and Prives, 1996, Genes & Develop. 10:1054–72). p53 is the most commonly mutated gene in cancer cells (Donehower et al., 1992, Nature 356:215–21; Vogelstein, 1990, Nature 348:681–682) and mutations in p53 are known to increase cell proliferation and promote chromosomal instability (Harvey et al., 1993, Oncogene 8:2457–67).

The early lethal phenotype in $rad51^{M1}$ mutant embryos and cells may be stimulated by a cell cycle response to unrepaired DNA damage. DNA damage was shown to inhibit progression through the cell cycle, demonstrating a relationship between DNA lesions and cell cycle proteins (Carr and Hoekstra, 1995, Trends in Cell Biology 5:32–40). In mitotically dividing budding yeast cells, a single DSB in a dispensable plasmid was sufficient to induce cell death, partly under the control of Rad9 (Bennett et al., 1993, Proc.

Natl. Acad. Sci. USA 90:5613–17; Schiestl et al., 1989, Mol. Cell. Biol. 9:1882–9654, Weinert and Hartwell, 1988, Science 241:317–22). In mammalian cells, the tumor suppressor gene, p53, responded to DNA damage induced by γ-radiation by delaying the cell cycle, or inducing programmed cell death (Kastan et al., 1991, Cancer Research 51:6304–11; Kuerbitz et al., 1992, Proc. Natl. Acad. Sci. USA 89:7491–95). These responses may be the critical tumor suppressor function of p53 (Baker et al., 1990, Science 249:912–15; Lowe et al., 1994, Science 266:807–10, Symonds et al., 1994, Cell 78:703–11). Induction of p53 after exposure to ionizing radiation and restriction endonuclease suggest that the formation of DSB may initiate a p53 response (Lu and Lane, 1993, Cell 75:765–78).

p53 was at least partly responsible for regulating the rad51$^{M1}$ phenotype because development was extended from the early egg cylinder stage to the head fold stage in a p53-mutant background. However, the double-mutant embryos died from either accumulation of DNA damage resulting in metabolic incompetence and mitotic failure, or p53-independent regulation. Murine embryonic fibroblasts, generated from double-mutant embryos, failed to proliferate and were completely senescent in tissue culture; thus, demonstrating that MmRad51 function was critical in cells that exhibit chromosomal instability and accelerated proliferation. It is therefore likely that disruption of MmRad5 or any other protein in its pathway or disruption of any protein—protein interaction important in the DSB repair pathway results in reduced proliferation or decreased cell viability. This feature remains true even in cells with reduced capacity to regulate the cell cycle.

The present invention is further illustrated by the following examples, which are not intended to be limiting in any way whatsoever.

5.0. EXAMPLES

5.1. Cloning of the Mouse MmRAD51 cDNA

The MmRAD51 cDNA sequence was cloned and used to generate an expression vector. The 5' end of cDNA was amplified by RT-PCR from mouse testis RNA and was then used as a probe to screen a mouse brain cDNA library. One clone was identified and sequenced. The coding sequence was identical to MmRAD51 disclosed in published reports (Morita et al., 1993; Shinohara et al., 1993); however, the clone contained about 300 additional base pairs of 5' non-coding sequence and about 400 extra base pairs of 3' noncoding sequence (FIG. 1).

5.2. The Use of a Yeast Two-Hybrid Screen to Isolate Proteins That Associate with MmRad51

ScRad51 was shown to self-associate as well as associate with other proteins such as ScRad52 and ScRad55 (Donovan et al., 1994; Hays et al., 1995; Johnson and Symington, 1995; Milne and Weaver, 1993; Shinohara et al., 1992). Kluyveromyeces lactis RAD51 and RAD52 did not rescue a rad51Δ rad52Δ strain of S. cerevisiae and overexpression of ScRAD51 suppressed rad55 and rad57 mutant yeast which indicates interacting proteins are necessary (Donovan et al., 1994; Hays et al., 1995). Also, Dmc1 and ScRad51 colocalized to the synaptonemal complex which suggested that they act together during meiotic recombination (Bishop, 1994).

The modified yeast two-hybrid system was used to isolate proteins that associate with mammalian Rad51 which is a genetic screen for determining protein—protein interactions (Harper et al., 1993). One of the proteins is a hybrid of the GAL4 DNA-binding domain fused to MmRad51 (the "bait"). The other is a hybrid of the GAL4 transactivating domain fused to an embryonic or a T cell cDNA library (the "prey"). The bait and prey were co-expressed in HF7c yeast that contained two reporters, HIS3 and lacZ fused to the GAL4 promoter and grown in media lacking histidine and containing 25 mM 3-AT (an antimetabolite; 3-amino-1,2,4-triazole)-Functional GAL4 was created when the DNA binding domain and the transactivation domain were juxtaposed, ideally by a MmRad51-protein interaction. Such an interaction induced the HIS3 and lacZ genes allowing a positive colony to survive in medium lacking histidine and to turn blue in X-Gal (5-bromo-4-chloro-3-indolyl-β-D-galactosidase).

Seven specific clones were isolated from this screen. A 13.5 day embryonic cDNA library (500 μg) was transfected into 5×10$^6$ cells and plated onto forty 15 cm plates. A T cell cDNA library (400 μg) was transfected into 4×10$^6$ cells and plated onto twenty 15 cm plates. A total of 80 His$^+$ colonies grew in about 3 days. Of these, 40 turned blue after about 5 to 30 minutes of exposure to X-gal. These colonies were tested for specificity by transfecting HF7c cells without bait or with a nonspecific bait (E12). Nonspecific associations were observed in 20 clones. The inserts in the other clones were sequenced and 13 were out of frame and seven were in frame. The sequences for the remaining seven clones were screened in the GCG data base. Homologues were found for four clones and three clones were novel (Table 1). The protein produced by clone 1 was 100% homologous to MmRad51 which showed that the screen was successful because RecA and ScRad51 are both known to self-associate. The protein produced from clone 2 was 100% homologous to a metal response element binding protein, M96 (Inouye et al., 1994, DNA and Cell Biol. 13(7): 731–742). The function of M96 is unknown. The protein produced from clone 3 was 48% homologous to human XP-G (ERCC-5) and 45% homologous to chicken Histone Hi. A mutation in XP-G is responsible for the genetic disorder xeroderma pigmentosum (Cleaver, 1994; Cleaver and Kraemer, 1995, In The metabolic basis of inherited disease, p. 4393–4419, 7th ed. McGraw-Hill, New York.). XP-G is a homologue of the S. cerevisiae excision repair protein, ScRad2 which is a ssDNA endonuclease. It is possible that MmRad51 repairs single-strand breaks as well as double-strand breaks and that single-strand breaks can initiate recombination. Histone H1 is a component of the nucleosome and comprises a group of related proteins that vary in tissues and are poorly conserved across species. The length of DNA may be affected by Histone Hi binding to the linker region and joining adjacent nucleosomes. The protein produced from clone 4 was 100% homologous to the human breast cancer gene, BRCA2 (Tavtigian et al., 1996, Nat. Gen. 12:333–337; Wooster et al., 1995, Nature 378:789–792). The function of Brca2 is unknown; however, like p53, it is a tumor suppressor gene and may therefore regulate the cell cycle in response to DNA damage. Thus, the observed association with a DNA repair gene, MmRad51, is consistent with such an activity.

TABLE 1

Clones isolated from the yeast two-hybrid screen

| Clone | Homology | Library |
|---|---|---|
| 1 | 100% to MmRad51 | T cell |
| 2 | 100% to M96 | embryo |
| 3 | 45% to Histone H1, 48% to XP-G | embryo |
| 4 | 100% to Brca2 | T cell |
| 5 | novel | T cell |

TABLE 1-continued

Clones isolated from the yeast two-hybrid screen

| Clone | Homology | Library |
|---|---|---|
| 6 | novel | embryo |
| 7 | novel | embryo |

Clones isolated from a yeast two-hybrid screen with MmRad51 as the "bait" and an embryonic or T cell cDNA library as the "prey". The inserts obtained from the prey were sequenced and compared to sequences in the GCG data base. The measured extent of protein homology is listed. All clones strongly associated with MmRad51 in the N-terminal region (amino acids 1–43). Colonies grew within three days in 3-AT, and cells generally stained blue after about 5 minutes of X-gal exposure.

5.3. Deletion Analysis of MmRad5 to Isolate the Protein Association Region

A deletion analysis was performed to isolate the MmRad51 self-association domain. Full length MmRAD51 was used as the bait and deletions of 51RAD51 were the prey (FIG. 2). The "prey" MmRad51 deletions were individually co-transfected with the bait into HF7c cells. The relative levels of β-galactosidase activity were measured for the MmRad51 deletion proteins as compared to full length MmRad51 which was considered to have 100% activity. Expression of the C-terminal region, TR43-339 and TR131-339 did not result in blue yeast cells after 10 hours, and the relative β-galactosidase activity was about 1, or the same as for the nonspecific bait, E12. However, expression of the N-terminal region, TR1-43, stained yeast cells blue in less than 5 minutes and the relative β-galactosidase activity was 43%. Interestingly, a sequence containing more of the N-terminal region of the protein, TR1-93, caused the yeast cells to stain blue after about 30 minutes of X-gal exposure, and reduced the relative β-galactosidase activity to about 4%. In similar experiments, TR1-131 and TR1-175 respectively displayed 11% and 9% of the β-galactosidase activity of the positive control. Nevertheless, these data indicated that the N-terminal region was responsible for MmRad51 self-association. It also appeared that amino acids 43–93 inhibited self-association and that this inhibition was relieved by adding more of the C-terminal region of the protein. These data indicated that MmRad51 was functionally conserved with ScRad51 since the self-association domain was also in the N-terminal region for both proteins even though these regions did not display conserved amino acid sequences.

The other six proteins listed in Table 1 were tested to determine if they interacted with the N-terminal region of MmRad51. All six strongly interacted with TR1-43; thus, the most N-terminal 43 amino acids were responsible for all the MmRad51 protein—protein interactions observed. Given the high level of homology shared between the human and murine Rad51 proteins (in the important N-terminal self-association region, the proteins only differ at amino acid positions 10 and 46 where the human sequence respectively contains an asparagine in lieu of the serine, and a phenylalanine in place of the tyrosine encoded by the mouse protein—both relatively conservative replacements), the presently described results should reflect the results expected from similar studies using the human Rad51 protein.

5.4. Transfection of Mouse Embryonic Stem Cells with Altered Alleles of Mammalian rad51

Both MmRad51 and ScRad51 self-associate using their respective N-terminal regions. This observation supports the hypothesis that these proteins remain functionally conserved. Functional conservation was further tested in the RecA core homology domain. In ScRad51, the RecA core homology region was shown to be essential for the repair of DSB. The gene rad51K-A191 was altered in the first ATP-binding motif, and a conserved Lysine was changed to an Alanine. The expression of rad51K-A191 in wild-type yeast cells dominantly impaired the repair of DNA damage and generated a rad51 null phenotype. Nonproductive protein—protein interactions were probably responsible for the dominant negative phenotype because rad51K-A191 was shown to associate with wild-type ScRad51 and ScRad52. If the MmRad51 structural domains were similar to ScRad51, then disruption of the conserved Lysine in the first ATP-binding motif should result in a null phenotype because of the nonfunctional associations with wild-type MmRad51 or other proteins in this pathway such as mouse Rad52 or Brca2. A null rad51 mutation resulted in a severe cell proliferation defect that prevented propagation of mutant mouse cells in tissue culture. Therefore, cells that expressed a dominant negative rad51 allele should not be recovered due to this proliferation defect.

Altered alleles of mammalian rad51 that were engineered to be dominant negative were expressed in mouse embryonic stem cells. Due to the severity of the null phenotype, these experiments were designed to measure the absence of transfected cells by statistically relevant numbers. The first experiment measured the transfection efficiencies of vectors that expressed altered mammalian rad51 as compared to a vector that expressed wild-type mammalian RAD51, or vector alone. The altered transgenes, rad51TR1-131 and rad51K-A134, contained a functional protein binding region and a nonfunctional RecA homology region. For rad51TR1-131, a C-terminal truncation was made in the first ATP-binding domain (FIG. 1). For rad51K-A134, the conserved Lysine in the first ATP-binding motif was changed to an Alanine (for review, see Donovan and Weaver, 1994). rad51K-A134 more strongly associated with full length MmRad51 than rad51 TR1-131 as measured using the yeast two-hybrid system with about 90% relative β-galactosidase activity (FIG. 1). The altered and wild-type transgenes were cloned into a CMV expression vector with a neomycin phosphotransferase (neo) cassette (pcDNA3 from invitrogen). Transfected embryonic stem (ES) cells were selected in G418 and colonies were counted 9 days later. The altered transgenes generated 20–30% fewer G418$^r$ colonies as compared to colonies resulting after transfection with wild-type MmRAD51 or vector alone in three experiments. Variations of 20–30% in transfection frequencies are commonly observed and are consequently not determinative in and of themselves. However, this minimal reduction could also indicate that the toxic product of the altered transgenes was produced in sufficient quantities to stop cell proliferation. However, if the transgene product was truly toxic, then why did 70–80% of the cells survive in selection media? The transgene may be silent while the neo gene is expressed. The transgene may be disrupted upon integration into the chromosome or by chromosomal positional effects. In addition, strong expression of the transgene may be required to observe a phenotype while only weak expression of neo may be required for positive selection. Another experiment was needed to circumvent these possible problems.

5.5. Targeting the Expression Vectors to the RPRT Locus

Another experiment was developed to compare the targeting frequencies of vectors that expressed altered mammalian rad51 with vectors that expressed wild-type mammalian RAD51 or MC1tk (Herpes Simplex Virus type 1 thymidine kinase). The transgenes were targeted to the hypoxanthine phosphoribosyltransferase locus, HPRT (Melton et al., 1984, Proc. Natl. Acad. Sci. USA 81:2147–2151). Targeting the transgenes to HPRT would decrease the likelihood of disruption upon integration and Southern analysis could also be used to verify the integrity of the integration event (FIG. 3). The transgenes would also be located to a favorable environment for expression since HPRT is a house keeping gene, and thus all of the transgenes would be affected to the same degree by chromatin positional effects. The transgenes were cloned into the bacterial plasmid of an insertion vector that targeted HPRT (IVH). There were 6.9 kb of HPRT sequences that contained a neo cassette in exon 3. Therefore, upon linearization using a unique site in the homology region (an engineered NotI site), both insertion and replacement events could be recovered.

The targeting vectors were linearized in the HPRT homology region and transfected into ES cells. Transfected cells were selected for by growth in medium containing G418, and targeted cells were selected in medium containing G418+6-thioguanine (TG). G418 resistant (G418$^r$) colonies were counted to measure the transfection efficiency and TG$^r$+G418$^r$ colonies were counted to measure the targeting frequency.

TABLE 2

Targeting frequencies

|  | Exp. | No. of Exps. | total G418$^r$ | total TG$^r$ | TG$^r$+ G418$^r$ | target frequency relative to IVH-tk |
|---|---|---|---|---|---|---|
| IVH-tk | A | 2 | 4088 | 338 | 1/12 | NA |
| IVH-51TA |  | 1 | 636 | 34 | 1/19 | −37% |
| IVH-51KA |  | 2 | 2792 | 106 | 1/26 | −54% |
| IVH-tk | B | 2 | 1200 | 124 | 1/10 | NA |
| IVH-51TA |  | 2 | 472 | 22 | 1/21 | −52% |
| IVH-51KA |  | 2 | 1504 | 62 | 1/24 | −58% |
| IVH-tk | C | 2 | 6016 | 264 | 1/23 | NA |
| IVH-51WT |  | 2 | 4840 | 192 | 1/26 | −12% |
| IVH-51TA |  | 2 | 2584 | 70 | 1/37 | −38% |
| IVH-51KA |  | 2 | 3664 | 48 | 1/76 | −70% |
| IVH-tk | D | 2 | 6744 | 414 | 1/16 | NA |
| IVH-51KA |  | 2 | 4848 | 136 | 1/37 | −57% |
| IVH-tk | E | 2 | 2624 | 186 | 1/14 | NA |
| IVH-51WT |  | 2 | 1456 | 84 | 1/17 | −18% |
| IVH-51TA |  | 2 | 2208 | 96 | 1/23 | −39% |
| IVH-51KA |  | 2 | 1376 | 52 | 1/26 | −46% |
| IVH-tk | F | 2 | 1664 | 156 | 1/11 | NA |
| IVH-51WT |  | 2 | 752 | 60 | 1/12 | −8% |
| IVH-51TA |  | 2 | 760 | 34 | 1/22 | −50% |
| IVH-51KA |  | 2 | 544 | 30 | 1/18 | −39% |

Table 2: Electroporation: 10 μg of NotI cut DNA/10$^7$ cells/ml PBS, 575 V/cm and 500 μF. Each experiment (exps. A—F) shows results from electroporations that were done on the same day with a common batch of ES cells under identical conditions to eliminate variability. NA, not applicable.

The targeting frequencies of vectors that contained altered rad51 alleles were compared to control vectors (Table 2). Vectors that contained altered rad51 alleles were IVH-51TR1-131 (contains rad51TRI-131) and IVH-51KA (contains rad51K-A134). Control vectors were IVH-51WT (contains wild-type MmRAD51), and IVH-tk (contains MC1tk). The relative targeting frequencies (TG$^r$+G418$^r$/G418$^r$ colonies) were determined using IVH-tk efficiency as 100%. The relative targeting frequencies were reduced by 13+/−3.6% for IVH-51WT (average of three experiments), 43+/−6.4% for IVH-51TR1-131 (average of 5 experiments) and 54+/−7.6% for IVH-51KA (average of six experiments).

Southern analysis was performed on TG$^r$+G418$^r$ clones to verify targeting and to identify the different targeting patterns (FIG. 3). Several types of recombination patterns were possible. A vector insertion event would integrate the entire vector to form a duplication of HPRT homology (Hasty et al., 1992, Molec. and Cell. Biol. 12:2464–2474). The vector may integrate on the 5' long arm or the 3' short arm (rarely observed). These integration patterns were combined since both integrate the transgene in between the duplication. A gene replacement event would introduce the neo but not the transgene and thus, provided a control. Modified events, that were not predicted by either pattern could also occur, and an intact transgene may or may not be introduced.

Comparison of the targeting patterns for the four vectors indicated that the transgene product was toxic for both rad51TR1-131 and rad51K-A134. The relative percentage of clones targeted with IVH-51TR1-131 and IVH-51KA that contained the transgene (vector insertion) decreased, and the relative percentage of targeted clones that did not contain the transgene (gene replacement) increased relative to controls. For both IVH-tk and IVH-51WT, targeting usually occurred by vector insertion (75% and 80%, respectively), rarely by gene replacement (14% and 17%, respectively), or more rarely by a modified event (6% and 8%, respectively). However, for IVH-51TR1-131 and IVH-51KA the relative frequency of targeted events that occurred by vector insertion decreased (68% and 45%, respectively), and gene replacement events increased (27% and 41%, respectively). The relative frequency of modified events also increased for clones targeted with IVH-51KA (14%). Therefore, the altered transgenes rarely integrated into the target locus as compared to the controls.

5.6. A High Percentage of Transfected Clones did not Express the Transgene

A statistically significant reduction in targeting frequency was observed using vectors that contained the altered rad51 alleles as compared to the wild-type allele or MC1tk. In addition, altered transgenes were introduced into HPRT for a lower percentage of the targeted clones as compared to the controls. However, targeted clones were generated that appeared to incorporate the altered transgenes intact. There are several possibilities for survival: 1) A small mutation may have been generated in the transgene; 2) The chromatin structure of the transgene may have been altered during the targeting event to silence the transgene (or vice- versa); 3) Position effect variegation may inhibit transcription of the transgene, but not neo.

Expression of MC1tk was tested in clones targeted with IVH-tk to determine the fraction of clones that do not express the transgene. Sixty-two TG$^r$+G418$^r$ clones were grown in replica plates, one without FIAU and one with FIAU, to distinguish clones that lost or maintained HSV-1 thymidine kinase activity. A large percentage of clones (42%) survived in FIAU demonstrating that the IVH-51TR1-131 and IVH-51KA targeting frequencies were reduced to background levels. Therefore, all of the cells targeted with either IVH-51TR1-131 and IVH-51KA that express the transgene were probably not recovered.

5.7. Conditional Expression of Amino Acids 1–43 of Mammalian Rad51 in ES cells Increases Sensitivity to γ-radiation It was demonstrated that the rad51$^{M1}$ mutation increases sensitivity to γ-radiation in early E3.5 day embryos and that dominant negative transgenes decrease proliferation of ES cells. Now, an expression vector that codes for amino acids 1–43 of Rad51 and is conditionally regulated by Doxycycline ("Dox") was introduced into the Hprt locus of ES cells. The expression vector is turned off by 5 ng/ml Dox. A vector that expresses the inducible tetR gene was transfected into the ES cells with the Rad51 1–43 expression vector in the presence of 5 ng/ml Dox. Ten clones were analyzed for sensitivity to γ-radiation when grown in media with or without Dox. Cells grown with Dox (transgene turned off) were more resistant to γ-radiation than cells grown without it, demonstrating that amino acids 1–43 of Rad51 sensitizes cells to radiation (FIG. 4a). Since ES cells are immortal and transformed, these data demonstrate that disrupting the Rad51 pathway will serve as a therapeutic for cancer. Therefore, expression of dominant negative transgenes that code for any protein that will disrupt mammalian Rad51 function could serve as a therapeutic for cancer and should not be limited to just the first 43 amino acids of Rad51.

5.8. Application of a Peptide that Inhibits Cell Proliferation by Disrupting Mammalian Rad51

It was demonstrated that mammalian Rad51 interacts with mammalian Brca2. A peptide of the amino acid sequence ROIKIWFONRRMKWKKFLSRLPLPSPVSPICTFV-SPAAQKAFQPPRS was synthesized. This peptide contains the region of Brca2 that interacts with Rad51, amino acids 3196–3226 (not underlined), SEQ ID NO. 3. This peptide also contains 16 amino acids derived from the Drosophila Antennapedia protein (underlined) SEQ ID NO:4 that translocates through biological membranes. This peptide was added to media after p53$^{-/-}$ fibroblasts were plated at low concentration (100 cells/ 6 cm plate). Colonies were counted based on size as determined by the number of cells. The peptide caused a great reduction of colonies composed of 265 or greater cells (FIG. 4b). Thus, the peptide had a profoundly negative effect on cellular proliferation. The 16 amino acids derived from Antennapedia had no effect on the number of colonies at any size; therefore, the inhibitory affect was due to the Brca2 sequences. Since p53$^{-/-}$ cells are highly proliferative and commonly found in cancer, these data demonstrate that disrupting the Rad51 pathway will serve as a therapeutic for cancer. Therefore, any peptide that interacts with mammalian Rad$^{51}$ may inhibit proliferation of cells in tissue culture and could be used to inhibit the growth of cancer.

5.9. Application of Molecules that Disrupt Mammalian Rad51 and/or Rad52 Function for Cancer Therapeutics The rad51$^{M1}$ mutation reduces proliferation and promotes cellular senescence, even in a p53 mutant background. In addition, rad51 dominant negative alleles also display this phenotype by presumably forming nonproductive protein associations with Rad51 and other proteins like Rad52, M96 and Brca2. Therefore, it is likely that the disruption of mammalian Rad51, mammalian Rad52 (or any protein in the DSB repair pathway mediated by these proteins) will reduce cell proliferation or induce cell death, and thus be suitable as a cancer therapeutic. In addition, the disruption of any protein—protein association important for mammalian Rad51 function or mammalian Rad52 function will also reduce cell proliferation or induce cell death, and thus be suitable as a cancer therapeutic.

Additionally, dominant negative alleles of rad51 may be used to express cancer therapeutics that reduce cell proliferation or induce cell death. An expression vector that codes for a dominant negative rad51 allele may be introduced into cancer cells, or an mRNA that codes for a dominant negative rad51 allele may be introduced into cancer cells, or a dominant negative Rad51 protein may be introduced into cancer cells. Several examples of such dominant negative rad51 alleles are presently disclosed. Of these alleles, the protein encoded by rad51K-A131 appears to have the strongest self-association, and proved toxic to proliferating cells. In fact, any rad51 allele that rendered the RecA homology region nonfunctional but preserved the N-terminal protein association region should reduce cell proliferation or induce cell death and could thus be used as a cancer therapeutic.

In addition to subtle alterations in the RecA core homology region of mammalian Rad51, C-terminal truncations in mammalian rad51 may also be used to reduce cell proliferation and/or induce cell death. rad51TR1-131 demonstrated a toxic effect on cells even though it had a relatively weak interaction with MmRad51 which suggested that the phenotype might be caused by nonfunctional self-associations, or nonfunctional associations with other proteins such as Rad52, M96 and Brca2. rad51TR1-43 had a strong interaction with MmRad51 and may be more effective as a cancer therapeutic than rad51TR1-131. In fact, any C-terminal truncation that preserves the protein interacting region of Rad51 may be used as a dominant negative allele for cancer therapy. Additionally, fusion of the N terminal domain of mammalian Rad51 to the 16 or 60 amino acids of the 3rd helix of the antennapedia protein may promote entry into the nucleus (Derossi et al., 1994, J. Bio. Chem. 269:10444–10450).

Mammalian Rad51 interacts with other proteins besides itself, and disruption of these interactions could be used to reduce cell proliferation or induce cell death. Other proteins interacting with mammalian Rad51 include but are not limited to mammalian Rad52, Brca2 and M96.

The identification of other interacting proteins will further elucidate the pathway and present greater opportunities to disrupt this pathway for the purpose of hindering cell proliferation. Since mammalian Rad52 associates with mammalian Rad51 and other proteins (Park et al., 1996; Shen et al., 1996), dominant alleles of mammalian Rad52 may also hinder cell proliferation or induce cell death. Such alleles could also be used for cancer therapeutics. In fact, dominant alleles of any protein that associates with mammalian Rad51, Rad52 or any other protein in these pathways, may be expected to hinder cell proliferation or induce cell death. Thus, all of the above molecules collectively define a new class of therapeutic agents for the treatment of proliferative disorders, viral infection (especially HIV infection), and cancer.

EQUIVALENTS

The foregoing specification is considered to be sufficient to enable one skilled in the art to broadly practice the invention. Indeed, various modifications of the above-described methods for carrying out the invention, which are obvious to those skilled in the field of microbiology, biochemistry, organic chemistry, medicine or related fields, are intended to be within the scope of the following claims. All patents, patents applications, and publications cited herein are incorporated by reference.

What is claimed is:

1. The truncated Rad51 product encoded by rad51TR1-131.

2. The altered Rad51 product encoded by rad51K-A134.

3. A polypeptide encoded by a polynucleotide which hybridizes under stringent conditions to a second polynucleotide that is complementary to a nucleotide sequence that encodes the amino acid sequence of SEQ ID NO:1 from residue 1 through 131, said polypeptide inhibits cell proliferation.

4. The polypeptide of claim 3 wherein the nucleotide sequence encodes the amino acid sequence of SEQ ID NO:1 from residue 1 through 43, said polypeptide inhibits cell proliferation.

5. A polypeptide encoded by a polynucleotide which hybridizes under stringent conditions to a second polynucleotide that is complementary to a nucleotide sequence that encodes the amino acid of SEQ ID NO:3, said polypeptide inhibits cell proliferation.

6. A polypeptide consisting essentially of the amino acid sequence of SEQ ID NO:1 from residue 1 to 131.

7. A polypeptide consisting essentially of the amino acid sequence of SEQ ID NO:1 from residue 1 to 43.

8. A polypeptide consisting essentially of the amino acid sequence of SEQ ID NO:3.

9. A polynucleotide that encodes the amino acid sequence of SEQ ID NO:1 from residue 1 to 131.

10. A polynucleotide that encodes the amino acid sequence of SEQ ID NO:1 from residue 1 to 43.

11. A polynucleotide that encodes the amino acid sequence of SEQ ID NO:3.

12. A method of screening for compounds that hinder cell proliferation or that promote programmed cell death, comprising:

a) assaying for microsatellite formation in cells;

b) assaying for chromosome loss in cells; or c) assaying for the disruption of strand exchange in an in vitro assay.

* * * * *